(12) United States Patent
Olivo et al.

(10) Patent No.: US 11,493,448 B2
(45) Date of Patent: Nov. 8, 2022

(54) METHOD FOR DETECTING AN ANALYTE USING SURFACE ENHANCED RAMAN SPECTROSCOPY

(71) Applicant: Agency for Science, Technology and Research, Singapore (SG)

(72) Inventors: Malini Olivo, Singapore (SG); Jayakumar Perumal, Singapore (SG); Ghayathri Balasundaram, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 794 days.

(21) Appl. No.: 16/078,273

(22) PCT Filed: Feb. 22, 2017

(86) PCT No.: PCT/SG2017/050080
§ 371 (c)(1),
(2) Date: Aug. 21, 2018

(87) PCT Pub. No.: WO2017/146647
PCT Pub. Date: Aug. 31, 2017

(65) Prior Publication Data
US 2019/0056328 A1 Feb. 21, 2019

Related U.S. Application Data

(60) Provisional application No. 62/297,999, filed on Feb. 22, 2016.

(51) Int. Cl.
*G01N 21/65* (2006.01)
*G01N 33/543* (2006.01)
*G01N 33/574* (2006.01)

(52) U.S. Cl.
CPC ..... *G01N 21/658* (2013.01); *G01N 33/54373* (2013.01); *G01N 33/57449* (2013.01); *G01N 2333/47* (2013.01); *G01N 2333/4713* (2013.01)

(58) Field of Classification Search
CPC ............ G01N 21/658; G01N 2333/47; G01N 2333/4713; G01N 33/54373; G01N 33/57449; G01N 21/553; G01N 21/65
USPC ............................. 436/525, 164, 805; 435/28
See application file for complete search history.

(56) References Cited

U.S. PATENT DOCUMENTS

| | | | | |
|---|---|---|---|---|
| 5,334,502 | A * | 8/1994 | Sangha | A61B 10/0051 422/412 |
| 11,237,159 | B2 * | 2/2022 | Olivo | G01N 33/57449 |
| 2007/0141714 | A1 | 6/2007 | Sung et al. | |
| 2007/0155021 | A1 | 7/2007 | Zhang et al. | |
| 2011/0129860 | A1 * | 6/2011 | Karl | G01N 33/57419 435/7.92 |
| 2013/0023435 | A1 | 1/2013 | Kho et al. | |
| 2013/0050695 | A1 * | 2/2013 | Erickson | B82Y 30/00 356/301 |
| 2013/0242297 | A1 | 9/2013 | Thoniyot et al. | |

FOREIGN PATENT DOCUMENTS

| | | |
|---|---|---|
| WO | 2013180652 A1 | 12/2013 |
| WO | 2014137291 A1 | 9/2014 |

OTHER PUBLICATIONS

Perumal (2015) "SERS-based quantitative detection of ovarian cancer prognostic factor haptoglobin", Int J Nanomed 10:1831-1840 (Year: 2015).*
Yu (2014) Raman Spect 45: 75-81 (Year: 2014).*
Kim (2015) IEEE conference AIM p. 535 (Year: 2015).*
Peng (1992) Phy Bio 82: 696-699 (Year: 1992).*
International Preliminary Report on Patentability for International Application No. PCT/SG2017/050080 dated Sep. 7, 2018, pp. 1-8.
Extended European Search Report for European Patent Application No. 17 756 930.8 dated Jul. 25, 2019, pp. 1-8.
Perumal et al., "SERS-Based Detection of Haptoglobin in Ovarian Cyst Fluid as a Point-of-Care Diagnostic Assay for Epithelial Ovarian Cancer," Cancer Management and Research, vol. 11, 2019, pp. 1115-1124.
Yu et al., "A SERS-Active Enzymatic Product Used for the Quantification of Diseases-Related Molecules," Journal of Raman Spectroscopy, vol. 45, Issue No. 1, Dec. 26, 2013, pp. 75-81, See Abstract.
Perumal et al., "SERS-Based Quantitative Detection of Ovarian Cancer Prognostic Factor Haptogloblin," Internaitonal Journal of Nanomedicine, vol. 10, No. 1, Mar. 6, 2015, pp. 1831-1840.
Yu et al., "A SERS-Active Enzymatic Product Used for the Quantification of Diseases-Related Molecules," Journal of Raman Spectroscopy, vol. 45, No. 1, Dec. 26, 2013, pp. 75-81.
Goh et al., "Optimized Bi-Metallic Film Over Nanosphere SERS Substrate for Sensitive Detection of Folic Acid," Photonics Global Conference, Dec. 13, 2012, pp. 1-4.

(Continued)

*Primary Examiner* — Christopher L Chin
(74) *Attorney, Agent, or Firm* — Shackelford, Bowen, McKinley & Norton, LLP

(57) ABSTRACT

According to the present disclosure, a method for detecting an analyte using surface enhanced Raman spectroscopy (SERS) is provided. The method comprises (a) contacting one or more analyte-binding molecules with the analyte under conditions that allow binding of the analyte to the one or more analyte-binding molecules to form a first mixture, wherein the analyte is preferably haptogloblin and the analyte-binding molecule may comprise haemoglobin or is a haptogloblin antibody, (b) contacting a liquid reagent comprising a peroxidase substrate and a peroxide source with the first mixture to form a second mixture, while maintaining pH of the second mixture at 10 or less, (c) quenching the second mixture to form a third mixture, (d) optionally contacting the third mixture with a SERS-active substrate, and (e) detecting a surface enhanced Raman signal from the third mixture and/or a surface of the SERS-active substrate.

19 Claims, 11 Drawing Sheets

(56) References Cited

OTHER PUBLICATIONS

Fu et al, "Enhancement in SERS Intensity with Hierarchical Nanostructures by Bimetallic Deposition Approach," Journal of Raman Spectroscopy, vol. 43, No. 8, Dec. 22, 2011, pp. 977-985.
Kim et al., "Development of A Novel Low-Cost Au-Prints SERS Paper Substrate for Point-Of-Care Application," IEEE International Conference on Advanced Intelligent Mechatronics (AIM), Jul. 7, 2015, pp. 535-536.
Zhan et al., "A Sensitive Surface-Enhances Raman Scattering Enzyme-Catalyzed Immunoassay of Respiratory Syncytial Virus," Talanta, vol. 148, Oct. 27, 2015, pp. 308-315.
Owens et al., "Sensing of p53 and EGFR Biomarkers Using High Efficiency SERS Substrates," Biosensors, vol. 5, No. 4, Oct. 28, 2015, pp. 664-677.
Perumal et al., "Design and Fabrication of Random Silver Films as Substrate for SERS Based Nano-Stress Sensing of Proteins," RSC Advances, vol. 4, No. 25, 2014, pp. 12995-13000.
BBI Solutions, http://www.bbisolutions.com/support/featured-products/anionic-gold-nanoparticles, 2018, pp. 1-3.
Zhao et al., "Circulating Haptoglobin is an Independent Prognostic Factor in the Sera of Patients with Epithelial Ovarian Cancer," Neoplasia, vol. 9, No. 1, Jan. 2007, pp. 1-7.
Laing et al., "Quantitative Detection of Human Tumor Necrosis Factor $\alpha$ by a Resonance Raman Enzyme-Linked Immunosorbent Assay," Analytical Chemistry, vol. 83, No. 1, Jan. 1, 2011, pp. 297-302.
Porstmann et al., "Enzyme Immunoassay Techniques An Overview," Journal of Immunological Methods, vol. 150, 1992, pp. 5-21.
Liu et al., "Specific and Reversible Immobilization of Histidine-Tagged Proteins on Functionalized Silicon Nanowires," Nanotechnology, vol. 21, No. 24, 2010, pp. 1-7.
Gutierrez et al., "Dual-Label Time-Resolved Fluoroimmunoassay for Simultaneous Quantification of Haptoglobin and C-Reactive Protein in Meat Juice From Pigs," The Canadian Journal of Veterinary Research, vol. 76, No. 2, 2012, pp. 136-142.
Cheng et al., "Immunochemical Property of Human Haptoglobin Phenotypes: Determination of Plasma Haptoglobin Using Type-Matched Standards," Clinical Biochemistry, vol. 40, 2007, pp. 1045-1056.
Huang et al., "Chemiluminescent Image Detection of Haptoglobin Phenotyping after Polyacrylamide Gel Electrophoresis," Analytical Chemistry, vol. 76, No. 11, Jun. 1, 2004, pp. 2997-3004.
Tridelta Development Limited, "Phase"™ Haptoglobin Assay Cat. No. TP-801, 2010, pp. 1-6.
Moskovits, Martin, "Surface-Enhanced Raman Spectroscopy: A Brief Retrospective," Journal of Raman Spectroscopy, vol. 36, Nos. 6-7, 2005, pp. 485-496.
Anker et al., "Biosensing with Plasmonic Nanosensors," Nature Materials, vol. 7, Jun. 2008, pp. 442-453.
Camden et al., "Probing the Structure of Single-Molecule Surface-Enhanced Raman Scattering Hot Spots," J. Am. Chem. Soc , vol. 130, No. 38, 2008, pp. 12616-12617.
Qian et al., "In Vivo Tumor Targeting and Spectroscopic Detection with Surface-Enhanced Raman Nanoparticle Tags," Nature Biotechnology, vol. 26, No. 1, Jan. 2008, pp. 83-90.
Maiti et al., "Multiplex Targeted in Vivo Cancer Detection Using Sensitive Near-Infrared SERS Nanotags," Nano Today, vol. 7, No. 2, 2012, pp. 85-93.
Dinish et al., "Sensitive Multiplex Detection of Serological Liver Cancer Biomarkers Using SERS-Active Photonic Crystal Fiber Probe," Journal of Biophotonics, 2013, pp. 1-10.
Huang et al., "Nanoaggregate-Embedded Beads as Novel Raman Labels for Biodetection," Advanced Functional Materials, vol. 19, No. 2, 2009, pp. 242-248.
Mahajan et al., "SERS-Melting: A New Method for Discriminating Mutations in DNA Sequences," J. Am. Chem. Soc., vol. 130, No. 46, 2008, pp. 15589-15601.
Xu et al., "Immunoassay Using Probe-Labelling Immunogold Nanoparticles with Silver Staining Enhancement via Surface-Enhanced Raman Scattering," Analyst, vol. 129, No. 1, 2004, pp. 63-68.
Kho et al., "Frequency Shifts in SERS for Biosensing," ACS Nano, vol. 6, No. 6, 2012, pp. 4892-4902.
Wu et al., "Gold Colloid-Bienzyme Conjugates for Glucose Detection Utilizing Surface-Enhanced Raman Scattering," Talanta, vol. 70, No. 3, 2006, pp. 533-539.
Guarrotxena et al., "Antitags: Nanostructured Tools for Developing SERS-Based ELISA Analogs," Advanced Materials, vol. 22, No. 44, 2010, pp. 4954-4958.
Ruan et al., "Detection of Alkaline Phosphatase Using Surface-Enhanced Raman Spectroscopy," Analytical Chemistry, vol. 78, No. 10, May 15, 2006, pp. 3379-3384.
Langlois et al., "Biological and Clinical Significance of Haptoglobin Polymorphism in Humans," Clinical Chemistry, vol. 42, No. 10, 1996, pp. 1589-1600.
Melamed-Frank et al., "Structure-Function Analysis of the Antioxidant Properties of Haptoglobin," Blood, vol. 98, Dec. 15, 2001, pp. 3693-3698.
Sigma-Aldrich, "Product Specification," https://www.sigmaaldrich.com/content/dam/sigmaaldrich/docs/Sigma/Datasheet/2/h0138dat.pdf, one page.
Tabassum et al., "Elevated Serum Haptoglobin is Associated with Clinical Outcome in Triple-Negative Breast Cancer Patients," Asian Pacific Journal of Cancer Prevention, vol. 13, No. 9, 2012, pp. 4541-4544.
Matsumoto et al., "Clinical Application of a Lectin-Antibody ELISA to Measure Fucosylated Haptoglobin in Sera of Patients with Pancreatic Cancer," Clin Chem Lab Med, vol. 48, No. 4, 2010, pp. 505-512.
Wang et al., "Comparison of the Peroxidase-Like Activity of Unmodified, Amino-Modified, and Citrate-Capped Gold Nanoparticles," ChemPhysChem, vol. 13, No. 5, 2012, pp. 1199-1204.
McKeating et al., "An Investigation Into the Simultaneous Enzymatic and SERRS Properties of Silver Nanoparticles," Analyst, vol. 138, No. 21, 2013, pp. 6347-6353.
Marana et al., "Management of Adnexal Cystic Masses with Unexpected Intracystic Vegetations Detected During Laparoscopy," Journal of Minimally Invasive Gynecology, vol. 12, 2005, pp. 502-507.
R. Aroca, "Surface-Enhanced Vibrational Spectroscopy," John Wiley & Sons Ltd., Chichester, 2006, pp. 1-260, see one page description of book.
Written Opinion of the International Searching Authority for International Application No. PCT/SG2017/050080 dated May 9, 2017, pp. 1-6.

\* cited by examiner

METHOD FOR DETECTING AN ANALYTE USING SURFACE ENHANCED RAMAN SPECTROSCOPY

CROSS-REFERENCE TO RELATED APPLICATION

This application claims the benefit of priority of U.S. Patent Application No. 62/297,999 filed on 22 Feb. 2016, the content of which is incorporated herein by reference in its entirety for all purposes.

TECHNICAL FIELD

The invention refers to a method for detecting an analyte using surface enhanced Raman spectroscopy (SERS). The invention also refers to use of such a method.

BACKGROUND

Methods for detecting analytes have typically relied on the use of means such as fluorescence or radioactive biomarkers. Each of these has its own limitations. For instance, the use of radioactive labels requires safety and regulatory protocols to be strictly adhered to and the disposal of the resultant radioactive waste may be costly and hazardous. Meanwhile, fluorescent methods may suffer from background fluorescence which interferes with accurate detection/determination of the fluorescent label.

Analytes which may be of interest include, but are not limited to, proteins, entities associated with cause of diseases such as cancer, or any other biomolecules. One example of an analyte which may be of interest for detection is Haptoglobin (Hp). Haptoglobin belongs to a family of acute phase serum glycoproteins. It may be mostly generated by hepatocytes in the liver and in little amounts by skin, kidneys and the lungs. Under normal conditions, it may be either absent or present at very low levels.

However, Hp may increase significantly in response to acute infection, inflammation or trauma. Recent studies have shown that Hp may be elevated in the sera and ascetic fluid of pre-operative ovarian cancer patients and a decrease was observed in patients undergoing chemotherapy. Conventional methods involving enzyme catalyzed assays like enzyme-linked immunosorbent assay (ELISA) may be commonly utilized for detection and quantification of Hp in clinical laboratories.

In ELISA, activity of the enzyme attached to anti-haptoglobin antibody may consequently be measured by means of its reaction with a chromogenic substrate to generate a measurable signal, which may be correlated to the amount of Hp present in a sample. Other than ELISA, electrochemical impedance spectroscopy (EIS), time-resolved immune fluorometry, labour-intensive electrophoresis, chromogen staining or chemiluminescent imaging have also been reported for Hp quantification. These conventional methods tend to be very time consuming and labour intensive for clinical applications. This necessitates the development of a simple, robust analytical method (which may or may not be antibody free) to help clinicians in detecting and quantifying Hp protein in a short time.

Apart from the above, colorimetry kits may also be commercially available to quantify Hp. These colorimetric kits may exploit the peroxidase activity of haemoglobin-haptoglobin [Hb-Hp] complex but their sensitivity may be insufficient to help in exact quantification of Hp protein, thereby resulting in uncertainty when predicting whether a patient is in border line or acute phase. For instance, an antibody free colorimetric method ("PHASE"™ Haptoglobin Assay Cat. No. TP-801) which is available, is different from the above-mentioned ELISA method relying on primary and secondary antibodies. This colorimetric method may be based on inhibition of peroxidase activity of free haemoglobin at low pH. Hp present in a specimen may combine with Hb at low pH to preserve the peroxidase activity of the bound Hb. Preservation of the peroxidase activity of Hb may be directly proportional to the amount of Hp present in the specimen. This colorimetric method may then utilize the peroxidase activity of the [Hb-Hp] complex and indirectly quantify the amount of Hp protein present in the clinical samples.

While this colorimetric method possesses advantages such as being antibody-free and circumvents the major issue for reliability of data, it tends to suffer the drawback as mentioned above i.e. insufficient to help exact quantification of the Hp protein and time taken for analysis may even take up to an hour or more. Such situations are likely to render it difficult for clinicians to decide if they have to surgically remove a cyst, for example, and these call for an ultra-sensitive and easily quantifiable method to detect Hp, such as an improved colorimetric method which is faster and more reliable with lower detection limits.

In view of the above, there is a need to provide for an improved method for detecting an analyte that overcomes or at least alleviates one or more disadvantages as mentioned above.

SUMMARY

In a first aspect, the invention refers to a method for detecting an analyte using surface enhanced Raman spectroscopy (SERS), the method comprising
  a) contacting one or more analyte-binding molecules with the analyte under conditions that allow binding of the analyte to the one or more analyte-binding molecules to form a first mixture,
  b) contacting a liquid reagent comprising a peroxidase substrate and a peroxide source with the first mixture to form a second mixture, while maintaining pH of the second mixture at 10 or less,
  c) quenching the second mixture to form a third mixture,
  d) optionally contacting the third mixture with a SERS-active substrate, and
  e) detecting a surface enhanced Raman signal from the third mixture and/or a surface of the SERS-active substrate.

In another aspect, the invention refers to use of a method as disclosed above for detection and/or quantification of proteins, and/or screening, monitoring, and/or detecting ovarian cancer.

BRIEF DESCRIPTION OF THE DRAWINGS

The invention will be better understood with reference to the detailed description when considered in conjunction with the non-limiting examples and the accompanying drawings, in which:

FIG. 1A shows two SEM images of a bimetallic film over nanosphere (BMFON) and a schematic diagram of BMFON. The left SEM image is at a magnification of ×1700 with a scale bar of 10 μm. The right SEM image is at a magnification of ×25000 with a scale bar of 1 μm. The schematic diagram of FIG. 1A shows the cross-sectional view of a BMFON according to embodiments as disclosed herein.

FIG. 2A shows silver (Ag) nano-island substrate fabricated by e-beam evaporation method. The scale bar is 100 nm.

FIG. 2B shows aqueous Au colloids with 60 nm average diameter. The scale bar is 100 nm.

DETAILED DESCRIPTION

Figure 1A:
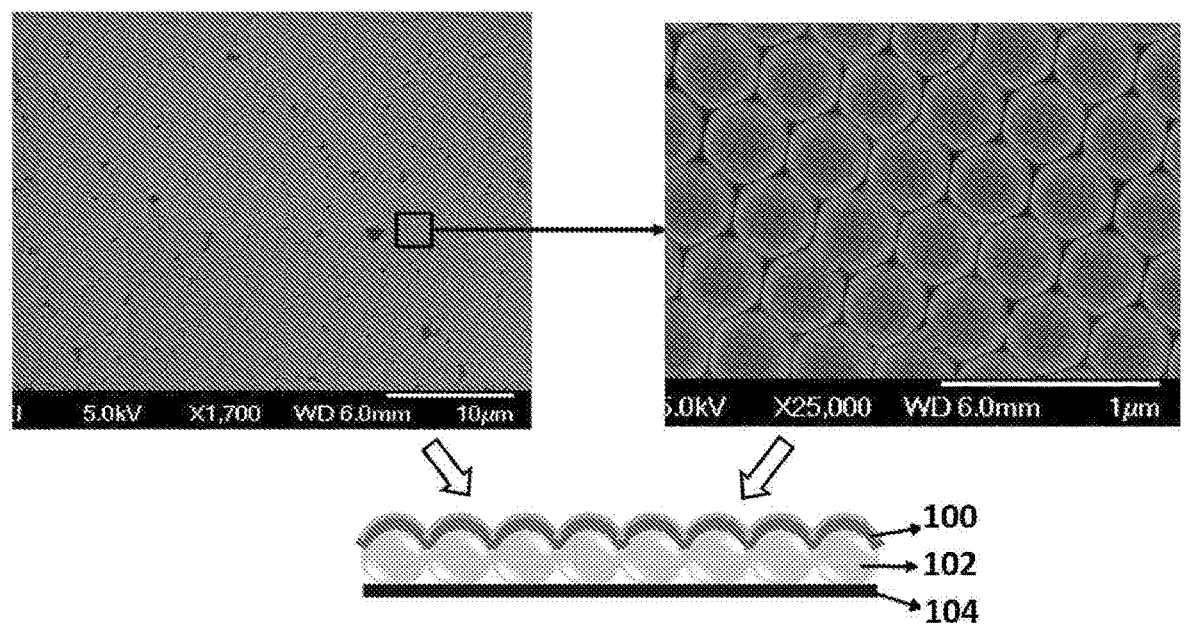
FIG. 1A shows field emission scanning electron microscope images (FESEM, also called SEM in the present disclosure) of bimetallic film over nanosphere (BMFON) used as one of the SERS substrates for Raman signal enhancement according to embodiments as disclosed herein. Specifically.

Various embodiments of the present disclosure refer to a method for detecting an analyte using surface enhanced Raman spectroscopy (SERS) and the use of such a method. The analyte may, for example, be haptoglobin. Various embodiments refer accordingly to a method for detecting haptoglobin (Hp) using surface enhanced Raman spectroscopy (SERS) and the use of such a method. Embodiments described in the context of the present method as disclosed herein are analogously valid for use of the present method for detection and/or quantification of proteins, and/or screening, monitoring, and/or detecting various forms of cancers (e.g. ovarian cancer).

By detecting presence and/or extent of peroxidase activity between an analyte and one or more analyte-binding molecules using SERS, detection and/or quantification of the analyte may be carried out. Advantageously, methods disclosed herein are based on surface enhanced Raman spectroscopy (SERS) which is a powerful vibrational spectroscopy technique for ultrasensitive bioassay because of advantages such as enhanced Raman signals by 10 to 14 orders of magnitude when a Raman active molecule comes into close proximity with a nano-roughened metal surface, and ultra-high sensitivity and ultra-high specificity with both made possible by molecular fingerprint information. Accordingly, the method disclosed herein may allow a more robust and efficient detection of the analyte, while providing higher sensitivity in detection as compared to traditional chromogenic tests. The method disclosed herein is also versatile as the one or more analyte-binding molecules may or may not be attached to a support, which may or may not be a SERS-active material.

In exemplary embodiments, the analyte is haptoglobin (Hp), while the analyte-binding molecule is haemoglobin (Hb). SERS may be employed to detect and quantify Hp based on the peroxidase activity of [Hp-Hb] complex to catalyze the reaction of a peroxidase substrate such as TMB and a peroxide source such as $H_2O_2$. By contacting haemoglobin with a sample suspected to comprise haptoglobin under conditions that allow formation of a haptoglobin-haemoglobin [Hp-Hb] complex to form a first mixture, and contacting a peroxidase substrate and a peroxide source with the resultant mixture, along with addition of a quenching agent and a SERS-active substrate, a surface enhanced Raman signal may be detected from a surface of the SERS-active substrate to allow detection of the haptoglobin. A principle behind this reaction may be that free haemoglobin (Hb) which exhibits peroxidase activity, is likely to be inhibited at a low pH. Hp present in the specimen or a test sample combines with Hb, and at a low pH preserves the peroxidase activity of the bound Hb. Preservation of the peroxidase activity of Hb may be directly proportional to the amount of Hp present. Hence, the peroxidase active [Hb-Hp] complex may oxidize a SERS inactive chromogenic reactant, such as but not limited to, 3,3',5,5'-Tetramethyl benzidine (TMB) (e.g. in the form of a liquid), into a SERS-active product $TMB^{2+}$. Enhanced sensitivity, improved analysis and quantification reliability with faster detection of acute phase protein and ovarian cancer biomarker Hp have been demonstrated herein.

On the above basis, the present method may utilize a combination of peroxidase reagents, which have unique Raman activity upon reaction with that of enzyme complex [Hb-Hp], and the use of specific non-toxic SERS platforms such as the specific composition of Au colloid or the use of specific SERS-active substrates for plasmonic enhancement by creating hot spots, sensitivity and reproducibility. Methods disclosed herein thus differ from methods for detection and quantification of protein biomarkers using SERS where antibodies are tagged to highly Raman active molecules, for example, malachite green isothiocyanate (MGITC), crystal violet (CV), rhodamine-6G, cyanine derivatives such as Cy3, Cy5 and DTTC, 4-mercaptobenzoic acid and p-aminothiophenol.

With the above in mind, various embodiments as disclosed herein relate to a method for detecting an analyte using surface enhanced Raman spectroscopy (SERS). The method may comprise contacting one or more analyte-binding molecules with the analyte under conditions that allow binding of the analyte to the one or more analyte-binding molecules to form a first mixture, contacting a liquid reagent comprising a peroxidase substrate and a peroxide source with the first mixture to form a second mixture, while maintaining pH of the second mixture at 10 or less, quenching the second mixture to form a third mixture, optionally contacting the third mixture with a SERS-active substrate, and detecting a surface enhanced Raman signal from the third mixture and/or a surface of the SERS-active substrate.

The term "detecting" as used herein refers to a method of verifying the presence of a given substance e.g. protein, molecule, and includes in vitro as well as in vivo detection. The detection may also be quantitative, such as correlating the detected signal with amount of analyte (e.g. Hp) present.

The terms "analyte", "target molecule" or "target" as interchangeably used herein, refer to any substance that can be detected via the present method using SERS by binding to an analyte-binding molecule, and which, in some embodiments, may be present in the sample. Therefore, the analyte can be, without limitation, any substance for which there exists a naturally occurring antibody or for which an antibody can be prepared. The analyte may, for example, be an antigen, a protein, a polypeptide, a nucleic acid, a hapten, a carbohydrate, a lipid, a cell or any other of a wide variety of chemical, biological or non-biological molecules, complexes or combinations thereof.

In the method as disclosed herein, one or more analyte-binding molecules may be contacted with the analyte under conditions that allow binding of the analyte to the one or more analyte-binding molecules to form a first mixture. The one or more analyte-binding molecules may be one that is suitable for binding to an analyte, and may specifically bind the analyte. The phrase "specifically bind", or its grammatical variants thereof, as used herein means that the analyte-binding molecule binds to the target analyte based on recognition of a binding region on the target analyte/molecule. In various embodiments, the analyte-binding molecules uniquely recognize and bind to the target analyte.

The present method is versatile as mentioned above because the one or more analyte-binding molecules may or may not be attached to a support according to various embodiments.

In various embodiments, the one or more analyte-binding molecules are not attached to a support. Analyte(s) that may be suitably detected using such a configuration may comprise or consist of haptoglobin (Hp). In these embodiments, suitable one or more analyte-binding molecules may comprise or consist of haemoglobin (Hb).

In various embodiments, the one or more analyte-binding molecules are attached to a support, which may or may not comprise a SERS-active material. As will be discussed later, depending on whether a SERS-active material is used in the support, a SERS-active substrate may be introduced in a subsequent step in a method for detecting an analyte disclosed herein.

In various embodiments, the support comprises or consists of a non-SERS active material. The non-SERS active material may be selected from the group consisting of an inorganic oxide particle having a magnetic core, a polymeric particle having a magnetic core, and/or combinations thereof. The non-SERS active material may also be selected from the group consisting of a silica particle having a magnetic core, a polystyrene particle having a magnetic core, and combinations thereof.

The particle, or more particularly the inorganic oxide particle, the polymeric particle, the silica particle or the polystyrene particle, may have a size in the range of about 100 nm to about 10 μm, about 150 nm to about 10 μm, about 200 nm to about 10 μm, about 500 nm to about 10 μm, about 1 μm to about 10 μm, about 5 μm to about 10 μm, about 100 nm to 5 μm, about 100 nm to about 1 μm, about 100 nm to about 500 nm, or other size range falling within any of these specified ranges. Accordingly, the particle may have a size in the range of about 100 nm to about 10 μm. The size may refer to an average size. The size may refer to the diameter of the particle. The term "diameter" may refer to the longest distance taken between two points on the external surface of an object, e.g. the particle, measured through the center of the object.

In various embodiments, the support comprises or consists of a SERS-active material. In these embodiments, the SERS-active material may comprise or consist of gold nanoparticles. Any other suitable nanoparticles applicable to the present method may also be used.

In embodiments where the one or more analyte-binding molecules are attached to a support, the analyte may comprise or consist of a protein. The protein may preferably comprise or may preferably be haptoglobin. Meanwhile, the one or more analyte-binding molecules may comprise or may be an antibody. The antibody may preferably comprise or may preferably be a haptoglobin antibody.

According to various embodiments as described above, the method as disclosed herein may be used, as a non-limiting example, for detecting an analyte comprising or consisting of haptoglobin (Hp) using surface enhanced Raman spectroscopy (SERS). In such instances, the method may comprise contacting haemoglobin with a sample suspected to comprise haptoglobin under conditions that allow formation of a haemoglobin-haptoglobin complex to form a first mixture, contacting a liquid reagent comprising a peroxidase substrate and a peroxide source with the first mixture to form a second mixture, while maintaining pH of the second mixture at 10 or less, adding a quenching agent to the second mixture to form a third mixture, contacting the third mixture with a SERS-active substrate, and detecting a surface enhanced Raman signal from the SERS-active substrate surface.

In various embodiments of the present method, the contacting of the one or more analyte-binding molecules (e.g. haemoglobin) with the analyte (e.g. a sample suspected to comprise haptoglobin) may be carried out for a time period in the range of about 2 minutes to about 10 minutes, about 3 minutes to about 10 minutes, about 4 minutes to about 10 minutes, about 5 minutes to about 10 minutes, about 6 minutes to about 10 minutes, about 7 minutes to about 10 minutes, about 8 minutes to about 10 minutes, about 9 minutes to about 10 minutes, about 3 minutes to about 9 minutes or any other duration within these specified ranges.

In various embodiments, the method as disclosed herein may further comprise adjusting pH of the first mixture to about 10 or less, about 9 or less, about 8 or less, about 7 or less, about 6 or less, about 5 or less, about 4 or less, about 3 or less, about 2 or less, or about 1 or less. In various embodiments, the pH of the first mixture may be adjusted to about 7 or less, or about 3 or less. In various instances, the pH of the first mixture may be adjusted to be in the range of about 2.6 to about 2.8, about 2.6 to about 2.7, or about 2.7 to about 2.8. Adjustment to a lower pH helps to enhance the SERS signal emitted by the SERS-active substrate.

In various embodiments, the pH of the first mixture may be adjusted by adding citric acid or citric acid/citrate buffer to the first mixture. The citrate buffer may comprise or consist of sodium citrate. In various instances, the citric acid/citrate buffer may be a citric acid/sodium citrate buffer.

The first mixture may be contacted with a liquid reagent comprising a peroxidase substrate and a peroxide source to form a second mixture, while maintaining pH of the second mixture at 10 or less. The first mixture, the liquid reagent comprising the peroxidase substrate and the peroxide source, or both the first mixture and the liquid reagent comprising the peroxidase substrate and the peroxide source may have the same or differing pH values so that pH of the resultant second mixture at 10 or less, such as 7 or less, 6 or less, 5 or less, 4 or less, 3 or less, or 2 or less. For example, at least one of the first mixture or the liquid reagent comprising the peroxidase substrate and the peroxide source may have a pH at 10 or less, such that pH of the resultant second mixture is 10 or less.

In embodiments wherein the analyte is haptoglobin (Hp), while the analyte-binding molecule is haemoglobin (Hb), for example, the liquid reagent comprising the peroxidase substrate and the peroxide source may be 3 or less, such as about 1 to about 3, about 2 to about 3, about 1 to about 2.5, about 1 to about 2, or about 1.5 to about 2.5. As mentioned above, the haemoglobin may not be attached to a support, and may accordingly be dispersed in the first mixture. The acidic pH of the liquid reagent comprising the peroxidase substrate and the peroxide source may be required to prevent undesired peroxidase reactions that give rise to false SERS results, in view that haemoglobin (Hb) may demonstrate peroxidase activity at a less acidic pH, such as a non-acidic pH or a pH greater than 3, even in the absence of Hp and/or when the Hb is not complexed with Hp. This may also be the case for other types of analyte-binding molecules capable of peroxidase activity at a less acidic pH, such as a non-acidic pH or a pH greater than 3.

The peroxidase substrate may be selected from the group consisting of 3,3',5,5'-tetramethylbenzidine, horseradish peroxidase, o-phenylenediamine, biphenyl-4,4'-dithiol, 5-bromo-4-chloro-3-indolyl phosphate, 2,2'-azino-bis(3-ethylbenzthiazoline-6-sulfonic acid), and combinations thereof. In some instances, the peroxidase substrate may comprise or consist of 3,3',5,5'-tetramethylbenzidine. In various instances, the peroxidase substrate may comprise or consist of 3,3',5,5'-tetramethylbenzidine, horseradish peroxidase, and combinations thereof. Advantageously, these peroxidase substrates, particularly 3,3',5,5'-tetramethylbenzidine, are non-toxic, which compares favorably with substrates such as o-phenylenediamine, biphenyl-4,4'-dithiol, and 5-bromo-4-chloro-3-indolyl phosphate which are toxic.

The peroxide source may be selected from the group consisting of hydrogen peroxide, carbamide peroxide, sodium perborate, sodium percarbonate, urea peroxide, and combinations thereof. Other peroxide sources which may be capable of releasing peroxide upon contact with an aqueous solvent, e.g. water, may be used. The peroxide source may comprise or consist of hydrogen peroxide.

pH of the second mixture may be maintained at 10 or less. As mentioned above, the first mixture, the liquid reagent comprising the peroxidase substrate and the peroxide source, or both the first mixture and the liquid reagent comprising the peroxidase substrate and the peroxide source may have the same or differing pH values to render pH of the resultant second mixture at 10 or less. Advantageously, adjustment to a lower pH helps to enhance the SERS signal emitted by the SERS-active substrate. In some embodiments, pH of the second mixture may be maintained at about 7 or less, about 6 or less, about 5 or less, about 4 or less, about 3 or less, about 2 or less. In some instances, the pH of the second mixture may be maintained in the range of about 2.6 to about 2.8, about 2.6 to about 2.7, or about 2.7 to about 2.8.

In the present method, the step of adding or contacting the liquid reagent comprising a peroxidase substrate and a peroxide source to the first mixture to thereby form the second mixture may be carried out under agitation. In some embodiments, the peroxidase substrate and the peroxide source are mixed prior to forming the liquid reagent. Agitation may take place via magnetic stirring, vortex mixing etc. Agitation may help to ensure proper mixing of the various components used to form the second mixture.

The step of contacting the liquid reagent comprising the peroxidase substrate and the peroxide source with the first mixture may be carried out for a time period in the range of about 1 minute to about 5 minutes, about 2 minutes to about 5 minutes, about 3 minutes to about 5 minutes, about 4 minutes to about 5 minutes, about 2 minutes to about 4 minutes, about 2 minutes to about 3 minutes, about 3 minutes to about 4 minutes, about 1 minute to about 3 minutes, or any other duration specified in these ranges.

In the present method as disclosed herein, the second mixture may be quenched to form a third mixture. Quenching of the second mixture may be carried out by at least one of heating the second mixture or adding a quenching agent to the second mixture.

In embodiments which utilize heating, the heating of the second mixture may be carried out at a temperature in the range of about 80° C. to about 95° C., about 85° C. to about 95° C., about 90° C. to about 95° C., about 80° C. to about 90° C., about 80° C. to about 85° C., or about 85° C. to about 90° C.

In embodiments where a quenching agent is utilized, the quenching agent may be selected from the group consisting of a strong acid, a free haemoglobin inhibitor, a protein binding inhibitor, a peroxide-reducing enzyme, and combinations thereof. In some instances, the quenching agent may be selected from the group consisting of hydrochloric acid, sulfuric acid, saponins, sodium dodecyl sulfate, cetyl trimethyl ammonium bromide, N-laurylsarcosine, dodecyltrimethylammonium bromide, 8-anilino-1-naphthalenesulfonic acid, protoporphyrin, bilirubin, taurodeoxycholic acids (bile salts), dicoumarol, 2-mercaptobenzothiazole, catalase enzyme, and combinations thereof. In other instances, the quenching agent may be selected from the group consisting of hydrochloric acid, sulfuric acid, catalase enzyme, and combinations thereof. In various instances, the quenching agent may comprise or consist of sulfuric acid. The advantage of selecting strong acids like HCl and $H_2SO_4$ etc. helps to denature the proteins such as the [Hb-Hp] complex upon contact with strong acids. Once the proteins are denatured, in this case the [Hb-Hp] complex, they are likely no longer involved in the peroxidase reaction.

The addition of the quenching agent to the second mixture or the quenching of the second mixture may be carried out under agitation. The various modes of agitation that may be employed are as described above.

The third mixture may optionally be contacted with a SERS-active (or written as a SERS active) substrate. As mentioned above, in embodiments wherein a SERS-active material is present, for example, as a support for attaching the one or more analyte-binding molecules, contacting of the third mixture with the SERS-active substrate may not be needed. Conversely, if a SERS-active material is not used or present in any preceding steps, such as during formation of the first mixture, the third mixture may be contacted with a SERS-active substrate to produce the SERS effects for improved detection.

For example, in embodiments where antibodies are utilized as the one or more analyte-binding molecules, the antibodies may already be attached to a SERS-active substrate/material such as gold nanoparticles, thus contacting the third mixture with the SERS-active substrate may not take place. In embodiments wherein antibodies are attached to a non-SERS active substrate/material, contacting the third mixture with a SERS-active substrate may be carried out. As a further example, formation of a [Hp-Hb] complex, which may take place in the absence of a support, may involve contacting the third mixture with the SER-active substrate.

In the present method as disclosed herein, the SERS-active substrate may comprise or consist of gold nanoparticles. The gold nanoparticles may be gold colloids. The gold colloids may be incorporated into paper substrates. The paper substrates may comprise chromatographic paper etc. The gold nanoparticles may be attached on a chromatographic paper. The SERS-active substrate may comprise or compose of other platforms, including but not limited to, bimetallic film over nanosphere(s) (BMFON), silicon nanopillars (SNP), and/or SERS paper substrate. The silicon nanopillars may be coated with a metal. The metal may be silver, gold or combination of both.

In embodiments where gold nanoparticles are used as the SERS-active substrate, the step of contacting the third mixture with the SERS-active substrate may comprise dispersing the gold nanoparticles in the third mixture. In these embodiments, the gold nanoparticles may be attached on a chromatographic paper.

Where gold nanoparticles are attached on a chromatographic paper, the step of contacting the third mixture with the SERS-active substrate may comprise dispersing the third mixture on the attached gold nanoparticles.

In embodiments where gold nanoparticles are used, the gold nanoparticles may comprise a size or diameter in the range of about 40 nm to about 80 nm, preferably about 50 nm to about 70 nm, more preferably about 60 nm.

In various embodiments, the SERS-active substrate may comprise a plurality of nanostructures attached on a support, and a first metallic layer deposited on the plurality of nanostructures. The SERS-active substrate may further comprise a second metallic layer deposited on the first metallic layer to form a metallic bilayer. The first metallic layer and the second metallic layer may be independently gold or silver. In some instances, the first metallic layer may be silver, and the second metallic layer may be gold. The nanostructures may be nanospheres or nanopillars.

In some embodiments, the step of contacting the third mixture with the SERS-active substrate may comprise dispersing the third mixture on the first metallic layer or the second metallic layer of the SERS-active substrate.

In the present method, detecting a surface enhanced Raman signal from the third mixture and/or the surface of the SERS-active substrate, may comprise detecting a change in pattern and/or intensity of SERS signal in the region of about 1100 $cm^{-1}$ to about 1700 $cm^{-1}$, about 1200 $cm^{-1}$ to about 1700 $cm^{-1}$, about 1300 $cm^{-1}$ to about 1700 $cm^{-1}$, about 1400 $cm^{-1}$ to about 1700 $cm^{-1}$, about 1500 $cm^{-1}$ to about 1700 $cm^{-1}$, about 1600 $cm^{-1}$ to about 1700 $cm^{-1}$, about 1200 $cm^{-1}$ to about 1300 $cm^{-1}$, about 1300 $cm^{-1}$ to about 1400 $cm^{-1}$, about 1600 $cm^{-1}$ to about 1700 $cm^{-1}$, or any other region within these specified ranges. In various instances, the step of detecting a surface enhanced Raman signal from the third mixture and/or the surface of the SERS-active substrate, may comprise detecting a change in pattern and/or intensity of SERS signal in the region of about 1600 $cm^{-1}$ to about 1650 $cm^{-1}$.

In the method as disclosed herein, the surface enhanced Raman signal from the third mixture and/or the surface of the SERS-active substrate may be correlated with amount of the analyte. The analyte may be contained in a sample and the detection may be in vitro. For example, the surface enhanced Raman signal from the SERS-active substrate surface may be correlated with the amount of haptoglobin.

In the method as disclosed herein, the concentration of the analyte (e.g. haptoglobin) in the sample is in the range of about 50 nM to about 40 µM, about 100 nM to about 40 µM, about 500 nM to about 40 µM, about 1 µM to about 40 µM, about 5 µM to about 40 µM, about 10 µM to about 40 µM, about 20 µM to about 40 µM, about 30 µM to about 40 µM, about 50 nM to about 30 µM, about 50 nM to about 20 µM, about 50 nM to about 10 µM, about 50 nM to about 5 µM, about 50 nM to about 1 µM, about 50 nM to about 0.5 µM, about 50 nM to about 0.1 µM, or about any other values within these specified ranges.

In the present disclosure, the sample may be a bodily fluid. The sample may also comprise a cultivated medium suspected of having the analyte (e.g. haptoglobin). The sample may comprise cyst fluid or suspected ovarian cancer cells.

The present method as described above may be used for detection and/or quantification of proteins, and/or screening, monitoring, and/or detecting various forms of cancer, such as but not limited to, ovarian cancer. The use of such a method may be done via a device that is compatible with and/or relies on the method as disclosed herein.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

As used herein, the term "and/or" includes any and all combinations of one or more of the associated listed items. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. While the methods described above are illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

Experimental Section

Surface enhanced Raman spectroscopy (SERS) is increasingly used for biosensing because of the high sensitivity and low detection limit that is made possible by the unique Raman 'fingerprint' spectra from the biomolecules. As disclosed herein, a modified SERS method for fast, sensitive and reliable quantitative analysis of analytes (e.g. haptoglobin (Hp)) has been developed. Hp is an acute phase plasma glycoprotein that is widely gaining application as a prognostic ovarian cancer biomarker. Accordingly, the sensitivity and reliability for analysis of analytes (e.g. Hp) have been enhanced in the present method as it incorporates SERS methodology into enzyme catalysis-based colorimetric bioassay to develop a more efficient and robust analytical protocol. Using this combination (i.e. colorimetric assay with SERS based quantitative analysis), a quick and simple detection method of analytes (e.g. Hp biomarker) in spiked serum was achieved.

For SERS platforms, both gold colloid and substrate platforms such as bimetallic film over nanosphere (BM-FON), silicon based nanopillars (SNP) with bimetallic coating and paper SERS substrates have been explored. The substrates shown in FIG. 1A to FIG. 1D are suitable for use as SERS substrate.

The modified SERS method as disclosed herein exploits the peroxidase activity of the haemoglobin-haptoglobin [Hb-Hp] complex, formed by selective and specific binding of Hp to free Hb to catalyze reaction of 3,3',5,5'-tetramethylbenzidine (TMB) substrate and hydrogen peroxide to result in the final product of a strong SERS-active $TMB^{2+}$. The strong SERS-active $TMB^{2+}$ was confirmed after testing various peroxidase substrates and their corresponding products for SERS activity. In addition, it is also less toxic compared to many other substrates tested.

A linear increase in the SERS signal of $TMB^{2+}$ was observed with increasing concentrations of [Hb-Hp] complex from 50 nM to 34 µM. Based on these concentration dependent SERS spectrums, Hp in clinical samples are quantified and analyzed. Inference about the prognosis of the disease coincided with histology data and the present method demonstrated more sensitivity than that of ELISA method. The results in the present disclosure also revealed that the method as disclosed herein has a detection range from 50 nM to 34 µM and a more sensitive detection limit compared to traditional chromogenic tests.

In summary, a SERS based assay with short reaction time, which can be potentially used for detection and quantification of Hp protein, is developed as disclosed herein.

Example 1

Materials

Chemicals were obtained from Aldrich and used as received. Haemoglobin, TMB, citric acid, bovine serum albumin (BSA) and PBS were purchased from Sigma-Aldrich. Hp antigens of human origin were purchased from Abcam. 60 nm Au colloid was obtained from BBI solutions, USA.

Example 2

Bimetallic Film Over Nanosphere (BMFON) Fabrication

Monodisperse polystyrene (PS) colloidal suspension (384 nm, 2.5 wt %) was purchased from Kisker. The glass slides/Si wafers were cleaned in ethanol and dried with argon gas. The PS sphere monolayers were prepared on these cleaned glass substrates by spin-coating method. Next, 10 ml of the prepared colloidal solution was dispersed onto the center of a glass slide. A spin coater was used to spin coat the PS colloidal suspension at 2000 rpm for 20 seconds. The sphere-templated substrates were then dried in a vacuum desiccator overnight. Finally, the substrates were coated with Au and/or Ag (99.999% purity, JEOL) at various thicknesses by sputtering technique (JEOL, JFC-1600 Auto fine coater). Each metal layer was deposited at a rate of 1.33 nm/s. The substrates of bi-metallic coating of Ag and Au are subsequently referred to as BMFON. FESEM images of the BMFON used for Raman signal enhancement and its cross-sectional view are depicted in FIG. 1A.

The cross-sectional view in FIG. 1A helps to explain the structure of BMFON. The glass or silicon wafer 104 serves as the underlying substrate on which a layer of PS beads 102 is spin coated. A layer of Ag or Au metal 100 is then coated over the layer of PS beads 102.

Example 3

Silicon Nanopillar (SNP) Fabrication

For fabrication of silicon nanopillars (SNP), silicon etch was performed using inductively-coupled plasma reactive ion etching system (ICP-RIE) from Oxford Instruments. Un-doped or P type silicon wafer can be used for SNP fabrication.

As a first step, the Si wafer was subjected to oxygen plasma treatment using $O_2$ gas under 10 to 15 mTorr chamber pressure for 5 minutes to 10 minutes based on the requirement of increasing the oxidized silica layer on the silicon surface.

Figure 1B:
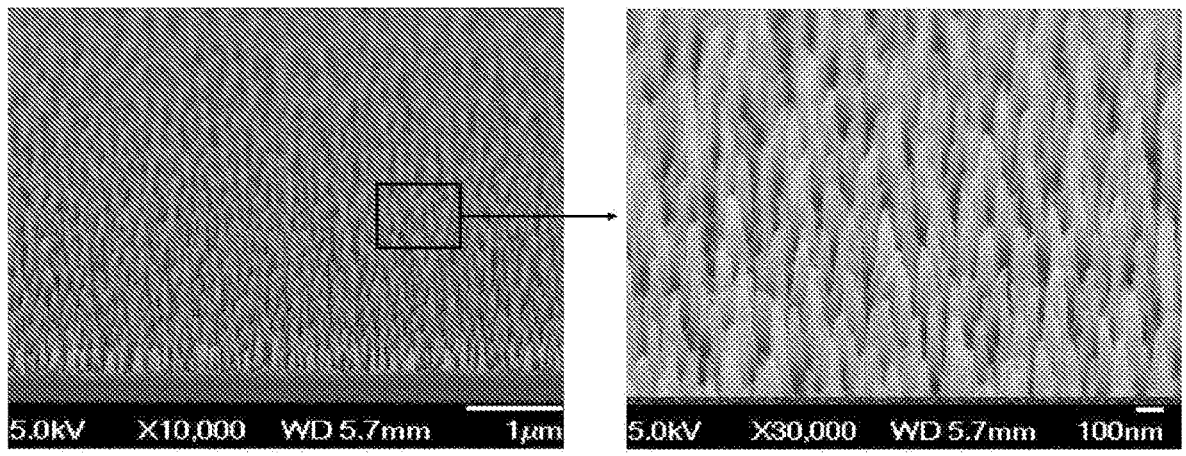
FIG. 1B shows two SEM images of silicon nanopillars (SNP) before metal coating. The left SEM image is at a magnification of ×10000 with a scale bar of 1 μm. The right SEM image is at a magnification of ×30000 with a scale bar of 100 nm.
Figure 1C:
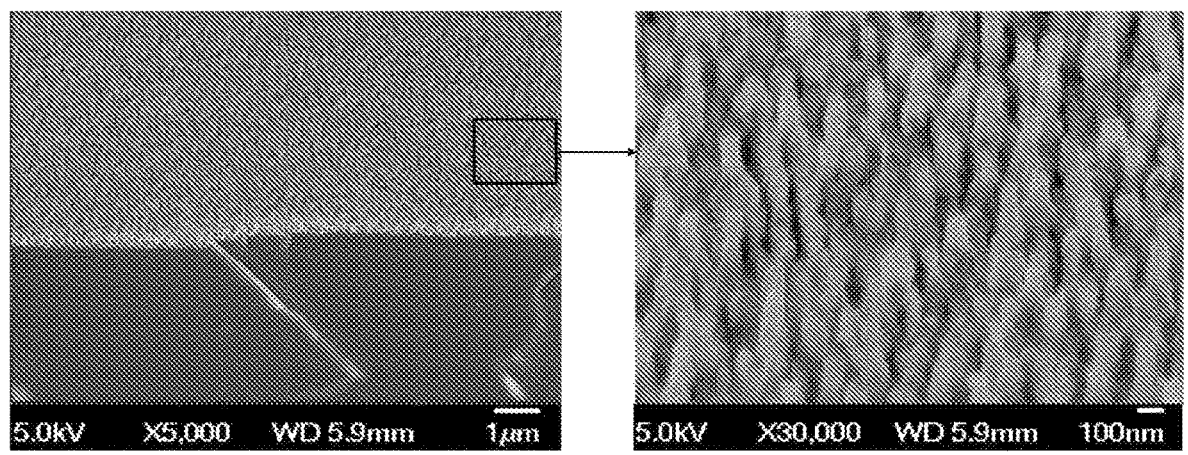
FIG. 1C shows two SEM images of SNP after metal coating. The left SEM image is at a magnification of ×5000 with a scale bar of 1 μm. The right SEM image is at a magnification of ×30000 with a scale bar of 100 nm. The SNP with metal coating can be used as one of the SERS substrates for Raman signal enhancement according to embodiments as disclosed herein.

In the second step, a combination of $SF_6:O_2$ gas was used in a ratio of 1.1 to 1.21 at an etch rate of 2.5 to 2.8 nm/s. As a final output, randomly arranged Si nanopillars with 250 to 300 nm height and a spacing (between the nanopillars) below 100 nm are obtained. FIG. 1B shows a FESEM image of bare SNP. Following this step, either only silver or a combination of silver and gold can be deposited by means of e-beam evaporation or sputtering process. FIG. 1C shows the FESEM image of SNP after depositing 200 nm silver by e-beam deposition process. The resultant SNP can be readily used for SERS study.

Example 4

Paper SERS Fabrication

Figure 1D:
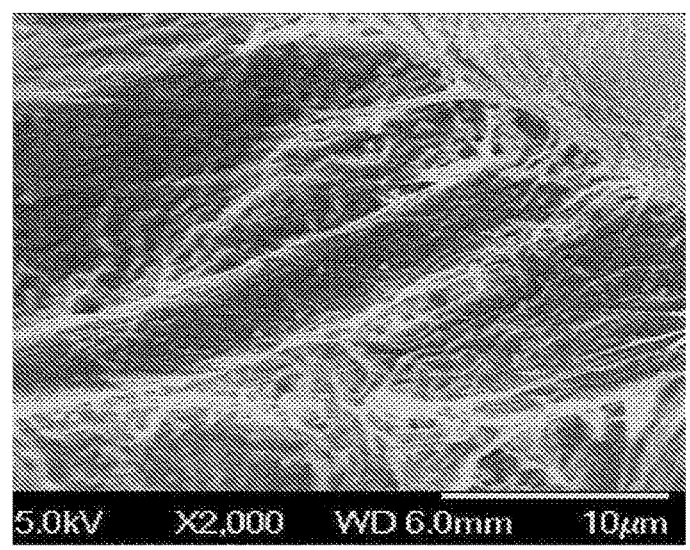
FIG. 1D shows a SEM image of gold (Au) colloid based paper SERS, or otherwise known as Au colloidal nanoparticles infiltrated into chromatographic paper, at a magnification of ×2000. The scale bar is 10 μm. The Au colloid based paper SERS or Au colloidal nanoparticles infiltrated into chromatographic paper can be used as one of the SERS substrates for Raman signal enhancement according to embodiments as disclosed herein.
Figure 2A:
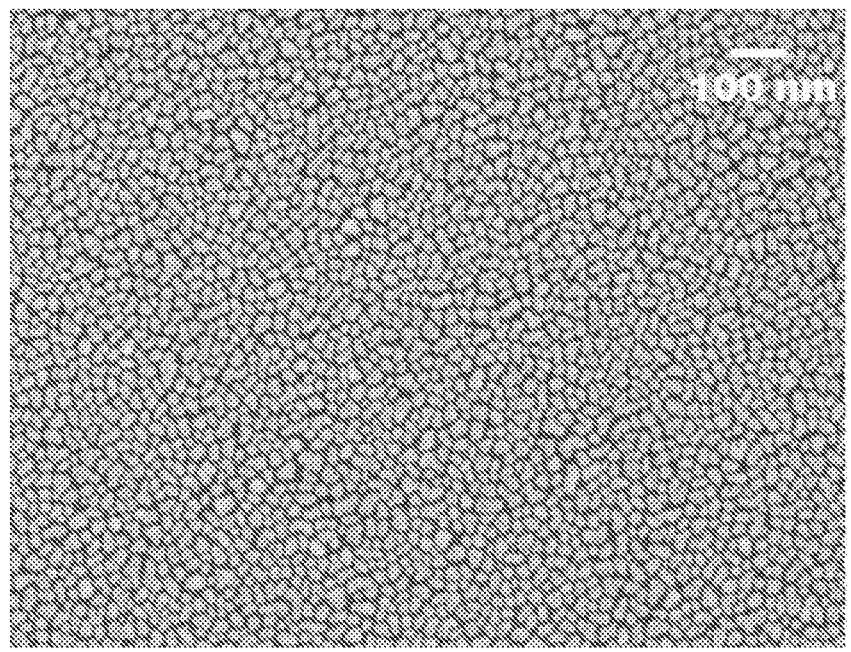
FIG. 2A shows a SEM image of one of the SERS substrates used in various embodiments as disclosed herein. Specifically.
Figure 2B:
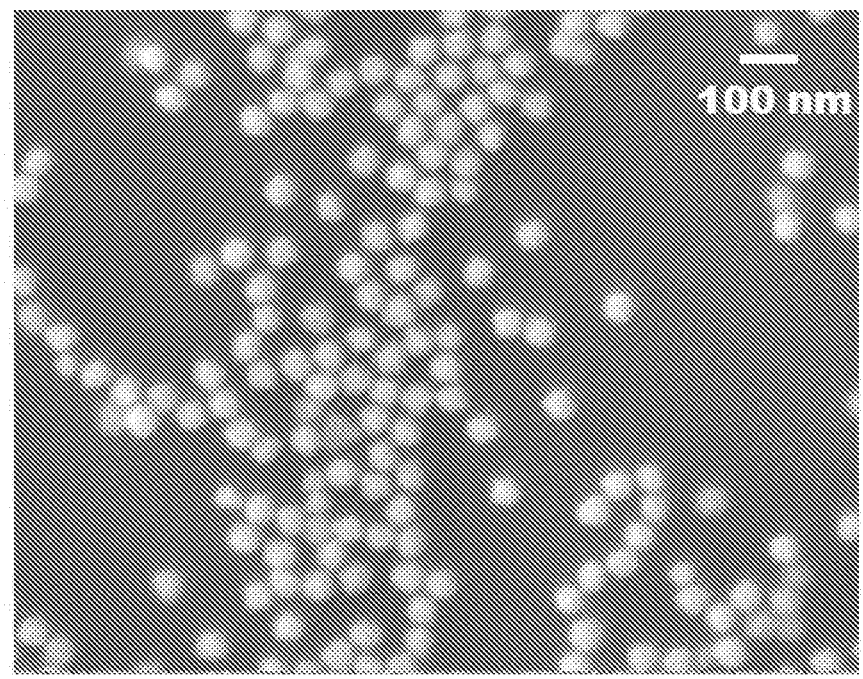
FIG. 2B shows a SEM image of one of the SERS substrates used in various embodiments as disclosed herein. Specifically.

In case of paper SERS fabrication process, Whatman chromatographic paper (from Sigma-Aldrich) was used. A method of using syringe filter to infiltrate Au colloidal nanoparticles into the chromatographic paper was employed as shown in FIG. 1D. Au colloids were used only in embodiments as illustrated by FIG. 1D. FESEM image of the Au colloids are shown in FIG. 2B.

Example 5

Preparation of [Hb-Hp] Complex

Hp can bind to Hb approximately in the ratio of 1:0.5 to 1:0.9 based on the information provided in reported works e.g. Sigma-Aldrich website. Using this information, to prepare a 3.3 mg/ml [Hb-Hp] complex, 3.3 mg of Hp and 2.97 mg of Hb were dissolved in 1 ml of 50% fetal BSA solution. The reaction time for [Hb-Hp] complex to form was around 5 minutes. Using this as stock solution, further dilutions were prepared up to 0.01 mg/ml by diluting with 50% fetal BSA solution and allowed to react for 30 minutes. The resultant [Hb-Hp] complex was stored in minus 20° C. until required for use. In the case of unknown clinical samples, the highest Hb concentration of 2.97 mg was dissolved into each of the clinical samples and allowed to react for 30 minutes; the resultant [Hb-Hp] complex was stored in minus 20° C. until required. Both Hb and Hp were of human origin obtained from Sigma-Aldrich and Abcam, respectively, as dry powder. The pH of TMB substrate was originally around 5.5 to 6.5. Since an acidic condition was needed, 0.1 M citric acid or sodium citrate buffer was added and dissolved to lower the pH to around 2.6 to 2.8.

The use of Hp to Hb in the ratio of 1:0.5 has also been explored. If the reaction needs to be quenched, strong acid can be used to stop the peroxidase reaction. Other different methods to quench the reaction may also be used. Some of the alternatives include heating to denature the enzyme or protein complex so that further reaction does not take place. In another instance, catalase can be used to consume the excess $H_2O_2$ present in the reaction medium. The reaction can also be quenched by eliminating any one of the reactants involved in the peroxidase reaction.

The product concentration from the peroxidase reaction is measured directly without the quenching step after certain fixed reaction time.

The minimum time needed for complex formation between Hb and Hp may take about 3 to 5 minutes. The volume of enzyme or protein complex to peroxidase reactant is 1 to 1 e.g. 10 µl of TMB/other peroxidase reactant is mixed with 10 µl of enzyme or protein complex. The reaction time can also be 2 to 3 minutes. This reaction time refers to the actual peroxidase reaction (i.e. the reaction time for mixing the first mixture with the second mixture).

A standard is always used when carrying out the present method with an unknown sample. The standard sample has a known concentration of enzyme or protein complex which undergoes the same experimental procedures as the unknown sample. The reaction occurs in parallel followed by UV absorbance and SERS reading taken. A microfluidic device is one of the most ideal platforms to carry out the parallel study for unknown and standard known samples.

The overall time (i.e. experimental and analysis) is shortened to less than 10 minutes. The overall time in this instance refers to or includes the duration for detection, quantification and analysis. By introducing microfluidic devices for diagnosis, reliability increases due to automation of the whole process by such devices.

Example 6

Procedures for Peroxidase Reaction Using [Hb-Hp] Complex

To perform reactions with different concentrations of [Hb-Hp] complex and the cyst fluid samples, 7.5 μl of TMB which was pre-dissolved with $H_2O_2$ (from Sigma-Aldrich) with pH of 2.6 to 2.8 was first prepared in an eppendorf tube. To this solution 1.5 μl of [Hb-Hp] complex/spiked serum was added and the reaction was allowed to proceed for 2 minutes in room temperature after mixing. At the end of 2 minutes, 7.5 μl of 0.5 M $H_2SO_4$ or 1 M HCl was added as stop solution and vortex well to stop the peroxidase reaction.

As an alternative approach, "catalase" enzyme (obtained from Sigma-Aldrich) as quenching agent can also be used since catalase helps in scavenging $H_2O_2$. Either the catalase can be used instead of strong acids or in combination with the strong acids to stop the peroxidase reaction. Before performing or in order to perform SERS measurements, either 45 μl of 60 nm Au colloid (from BBI solutions) was added to 10 μl of the above reaction mixture or 10 μl of the reaction mixture was dropped onto the SERS substrates prepared as described above (see examples 2 to 4).

For the SERS substrate approach, one of the substrate used was either BMFON or purely gold coated film over nanospheres (AuFON). As a second and more robust substrate, SNP with only gold coating on top of it or bimetallic coating, i.e. gold metal layer on top of silver, was also tested.

All the above substrates could be used for SERS study. SERS measurement could be done by simply dropping 4 to 5 μl of the reaction mixture onto the SERS substrate and measure the SERS spectra of $TMB^{2+}$.

Example 7

Clinical Sample Study

In the experiments, cyst fluid samples used for the study were from clinical specimens stored at minus 20° C. Specimens were used in accordance to procedures with approval of the local ethics committee with the protocol reference number (D2007/240). Informed consent was obtained from each subject.

Example 8

Raman Microscopy and SERS Measurements

For surface-enhanced Raman spectroscopy (SERS) measurements, two methods were employed. One was substrate based and the second was metal colloid based. For SERS substrate, an Ag nano-island on Si wafer with an average particle size ranging from 25 to 50 nm was used. For the metal colloids, commercially available 60 nm Au colloids were used. FIG. 2A and FIG. 2B shows the FESEM images of both substrate and metal colloids, respectively. FIG. 2A shows the FESEM image of Ag nano-island SERS substrate fabricated by e-beam evaporation method, which was used in the experiments. FIG. 2B shows the FESEM image of aqueous Au colloid with 60 nm average diameter used in the experiments.

SERS measurements were performed in reflection mode with a Raman microscope (Renishaw InVia) using a 633 nm excitation laser with 5% laser power, a 1800 line/mm grating and a cooled CCD (−70° C.). A 50× or 20× objective lens (NA 0.75 or 0.4, respectively) delivered the laser beam and collected the back scattered light. Rayleigh scattering was blocked with a notch filter. The laser spot size was about 1 or 3 μm with a power of 0.3 or 0.28 mW, respectively. Measurements were performed with a 10 second integration time. Measurements were taken at multiple positions across each SERS region and data was averaged. Background corrections and curve fittings were carried out using WiRE 3.2 or 3.4 (Renishaw software). Spectra were background subtracted by a 6-order polynomial fit before the curve-fitting procedure. The instrument is calibrated with signal from a silicon standard at 520 $cm^{-1}$.

Figure 3:
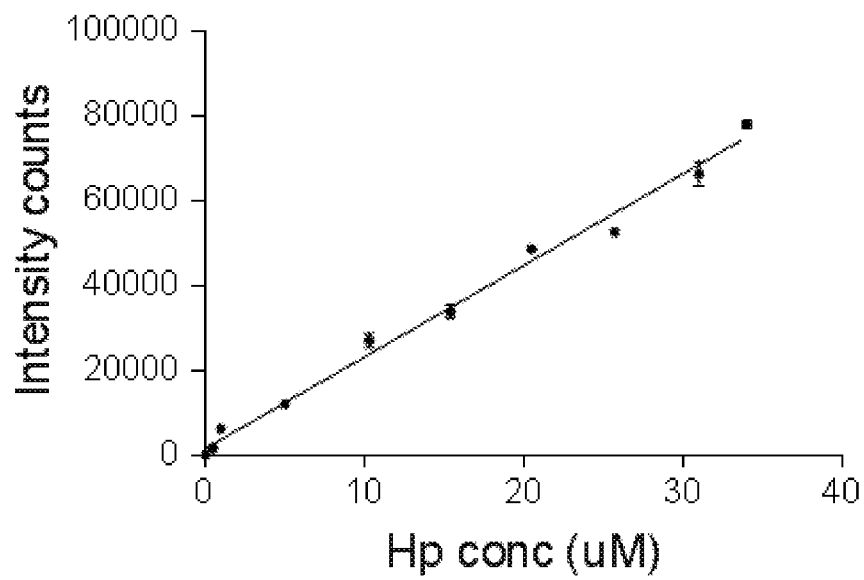
FIG. 3 is a calibration plot for different concentrations of Hp present in the [Hb-Hp] complex based on the intensity of 1605 cm$^{-1}$ peak. $R^2$ has a value of 0.98.

Calibration plot using different concentration of [Hb-Hp] complex with the fixed concentration of peroxidase substrate and $H_2O_2$ with their corresponding SERS product intensity recorded. The product intensity peak at 1605 $cm^{-1}$ was obtained by peroxidase reaction in presence of [Hb-Hp] complex. FIG. 3 shows a calibration plot for different concentrations (from 50 nM to 34 μM) of Hp present in the [Hb-Hp] complex based on the intensity of 1605 $cm^{-1}$ peak. As shown in FIG. 3, a calibration plot with linear regression having $R^2$ value of 0.98 was obtained.

Example 9

UV-Vis Absorbance Measurement

Figure 4:
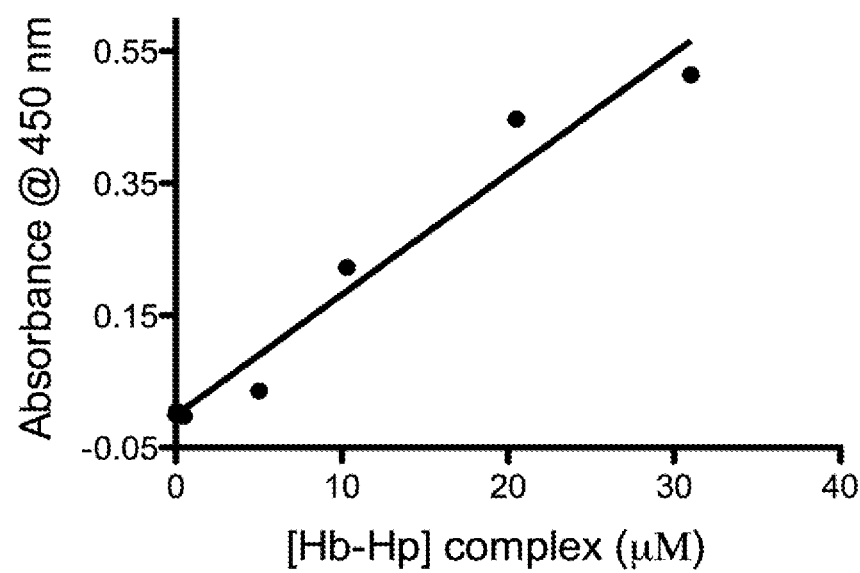
FIG. 4 shows the calibration plot of UV absorbance data for various concentrations of [Hb-Hp] complex, where the linear regression follows the equation, y=0.0182x and $R^2$ has a value of 0.96.

The wavelength-dependent absorption spectrum was measured using a DU 730, Beckman Coulter spectrophotometer system scanning between 250 to 800 nm. FIG. 4 shows the calibration plot of UV absorbance data for various concentrations of [Hb-Hp] (from 50 nM to 34 μM), where the linear regression follows the equation, y=0.0182x and $R^2$ has a value of 0.96.

Example 10

ELISA Calibration

A commercial enzyme-linked immunosorbent assay (ELISA) kit was purchased from Abcam for Hp quantification. Following the standard protocol given in the ELISA kit, a calibration plot was prepared based on the ultraviolet absorbance data (see FIG. 5).

Figure 5:
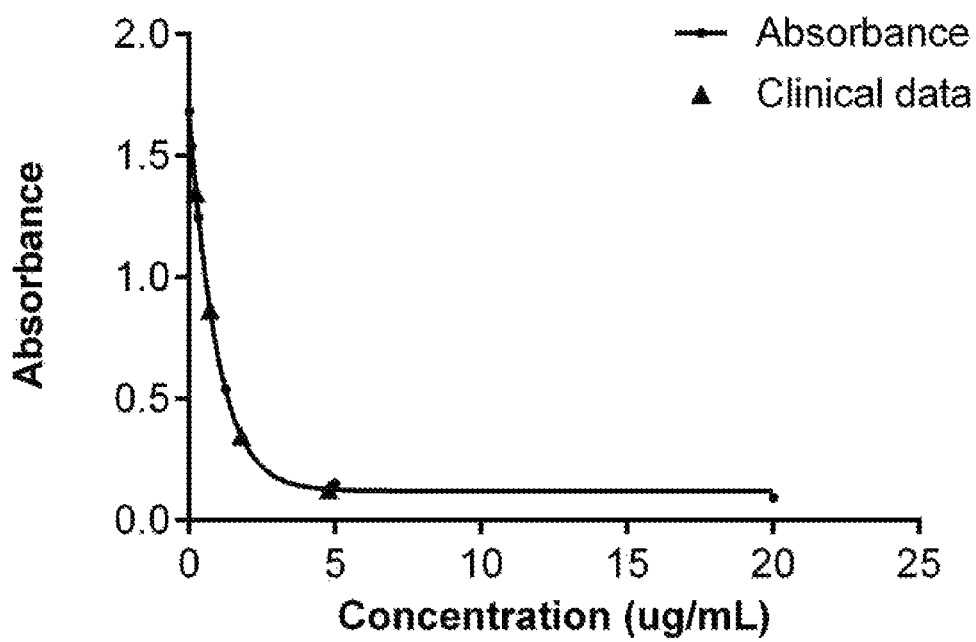
FIG. 5 shows an enzyme-linked immunosorbent assay (ELISA) calibration plot interpolated with clinical cyst fluid data.

Finally, clinical cyst fluid samples were run in the same way and the data were interpolated into the ELISA calibration plot to derive the concentration of Hp present in the various cyst fluid samples. Results are shown in FIG. 5 (i.e. ELISA calibration plot interpolated with clinical cyst fluid data).

Example 11

Results and Discussion For Colorimetric Detection of Hp

Haptoglobin has been detected in clinics by traditional enzyme-catalyzed reactions that involve the formation of a chromogen as a result of the reaction between the substrate and the enzyme. The chromogen is quantified by spectrophotometry based on intensity of light transmitted. Several chromogenic reactants that undergo instant oxidation by $H_2O_2$ in the presence of peroxidase enzymes are commercially available. Amongst them, 3,3',5,5'-tetramethylbenzidine (TMB) is one of the most widely used substrate because of its less toxicity and higher sensitivity than other reactants such as o-phenylenediamine (OPD) and 2,2'-azino-bis(3-ethylbenzthiazoline-6-sulfonic acid) (ABTS). Therefore, TMB was used as a peroxidase substrate for quantifying Hp via the peroxidase activity of the [Hb-Hp] complex in the presence of $H_2O_2$. One of the unique properties of the TMB reactant realized in this disclosure is that it has no SERS signal. Only upon peroxidase reaction in the presence of [Hb-Hp] complex is the SERS inactive TMB reactant converted to a SERS-active $TMB^{2+}$ product as shown in FIG. 6.

Figure 6:
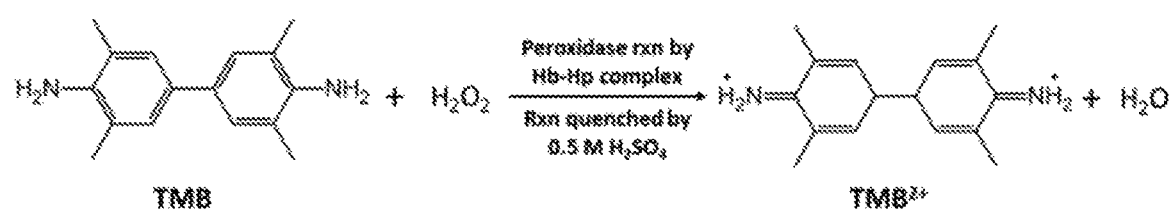
FIG. 6 shows the reaction scheme for the [Hb-Hp] enzyme catalyzed peroxidase reaction of TMB to TMB$^{2+}$.
Figure 7:
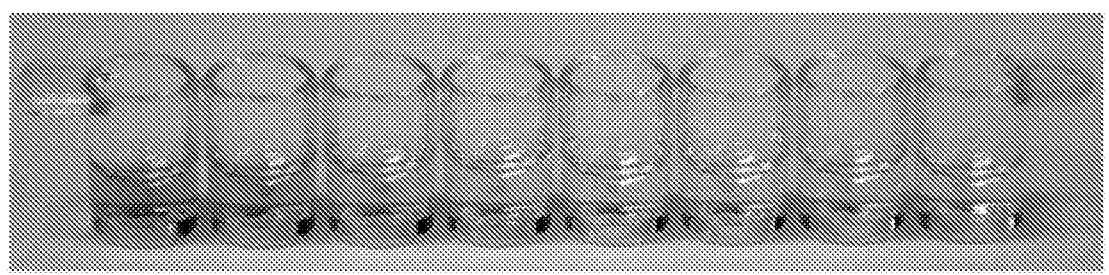
FIG. 7 shows optical images of fixed concentration of chromogenic reactant with different concentrations of [Hb-Hp] complex, starting from 31 μM [Hb-Hp] in the leftmost container to 0 μM [Hb-Hp] (blank) in the rightmost container.

The [Hb-Hp] complex-catalyzed oxidation of TMB by $H_2O_2$ proceeds via the two-step two-electron reaction as shown in FIG. 6, which depicts the reaction scheme for catalytic conversion of TMB to $TMB^{2+}$. The first step (one-electron oxidation) yields a radical cation which exists in rapid equilibrium with a blue charge transfer complex (CTC). Addition of a strong inorganic acid such as $H_2SO_4$ can terminate the reaction, yielding the yellow $TMB^{2+}$. At low pH due to addition of $H_2SO_4$, formation of the two-electron product is favorable. Both CTC and $TMB^{2+}$ can be quantified by spectrophotometer, thus providing a convenient means of detection. FIG. 7 represents the photographic image of the oxidized product $TMB^{2+}$ at different concentrations of [Hb-Hp] complex (optical image of fixed concentration of chromogenic reactant with different concentrations of [Hb-Hp] complex, starting from 31 µM [Hb-Hp] on the left to 0 µM [Hb-Hp] (blank) on the right). The intensity of yellow color decreases with decreasing concentration of the [Hb-Hp] complex with almost no color at a concentration of 5 µM or less (the yellow color intensity decreases starting from the left to right containers of FIG. 7).

Figure 8:
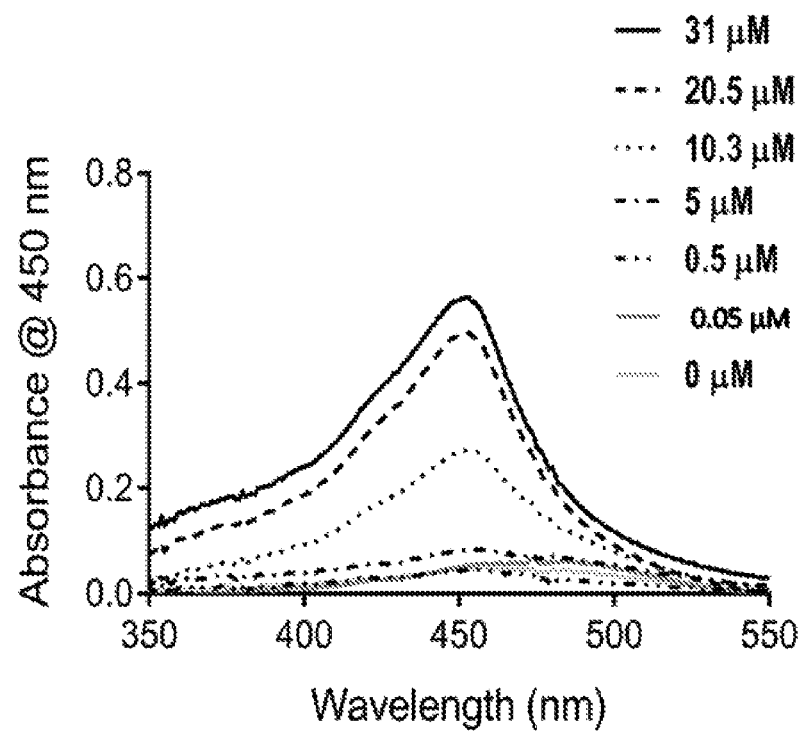
FIG. 8 shows the corresponding UV absorbance data for the samples of FIG. 7.

FIG. 8 shows the correlation of [Hb-Hp] complex concentration and UV absorbance data at 450 nm. According to FIG. 8, the corresponding UV-VIS spectra of the $TMB^{2+}$ at a wavelength of 450 nm also follows the same trend as the color results of the photographic images of FIG. 7. The lowest detection limit by this method was observed to be 5 µM after which the absorbance was almost same as the blank. This demonstrated that lower concentrations of Hp cannot be detected by the colorimetric method thus requiring highly sensitive method to quantify Hp.

Example 12

Results and Discussion For SERS Detection of Hp

As the concentration of Hp in ovarian cyst fluid is used as a marker for different types of cancer, in particular ovarian cancer, and is an essential factor for delineating cancerous ovaries from normal ones, there is a necessity for a highly sensitive detection and quantification method for determining the prognosis of the disease. Since TMB is known to possess strong Raman scattering property, Ag nano-island substrate as developed by the inventors could be used (see FIG. 2A).

Figure 9:
FIG. 9 shows a reaction scheme for SERS measurement.

Monitoring of stable SERS spectra upon peroxidase reaction by different concentrations of [Hb-Hp] complex was not possible. This was later confirmed to be due to auto-oxidation effect arising from continuous oxidation by Ag metal in the presence of $H_2O_2$ and in the absence of [Hb-Hp] complex. Upon repeating the experiments to collect multiple spectra, the signal intensity decreases drastically. This phenomenon of auto-oxidation of gold and silver was reportedly established by different research groups. Advantageously, gold coated structures or substrates comprising gold tend to be less- or non-susceptible to auto-oxidation compared to silver or other easily oxidized metals. Hence, substrates or structures on substrates coated with gold as the outer layer over silver inner layers tend to experience minimal auto-oxidation effects. Pure gold colloids tend to possess such an advantage over pure silver colloids. Hence, aqueous gold colloid with an average particle size of 60 nm (see FIG. 2B) was chosen for use with the oxidized product $TMB^{2+}$ to enhance the Raman signal and then the ultra-sensitive SERS modality was used to quantify the peroxidase activity of [Hb-Hp] complex and thus the concentration of Hp. The scheme for SERS measurement using gold (Au) colloid is shown in FIG. 9.

Figure 10:
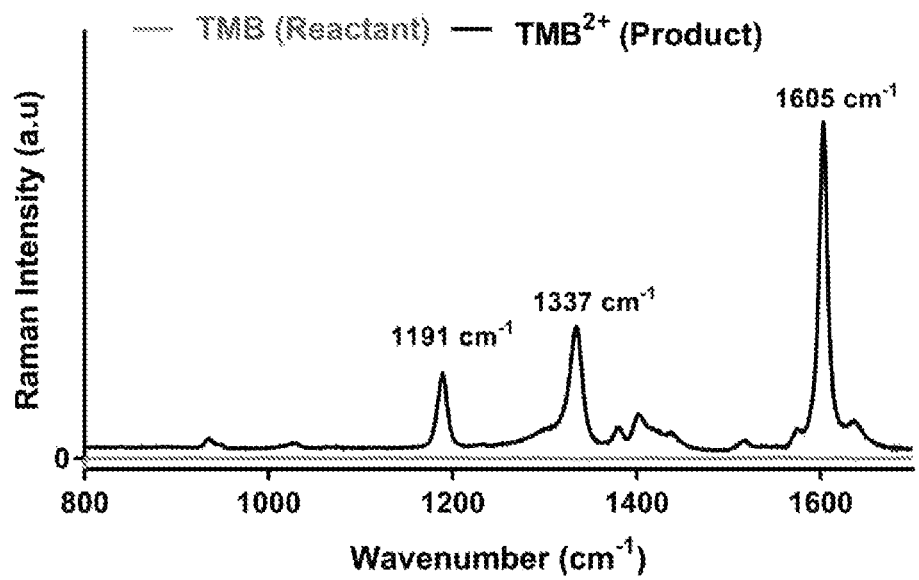
FIG. 10 shows the comparison of SERS spectra for both reactant TMB (denoted by the flat line) and product TMB$^{2+}$.

FIG. 10 represents a comparison of the SERS spectra of the reactant substrate TMB and its oxidized version $TMB^{2+}$. Bands or peaks at 1191, 1337, and 1605 $cm^{-1}$ were identified as the characteristic SERS bands of $TMB^{2+}$, as shown in FIG. 10. The peak at 1191 $cm^{-1}$ represents the characteristic $—CH_3$ bending mode, whereas peaks at 1337 and 1605 $cm^{-1}$ correspond to inter-ring stretching and a combination of ring stretching and CH bending vibrations, respectively. The SERS spectrum of the reactant substrate TMB in FIG. 10 is represented by the flat line.

Figure 11:
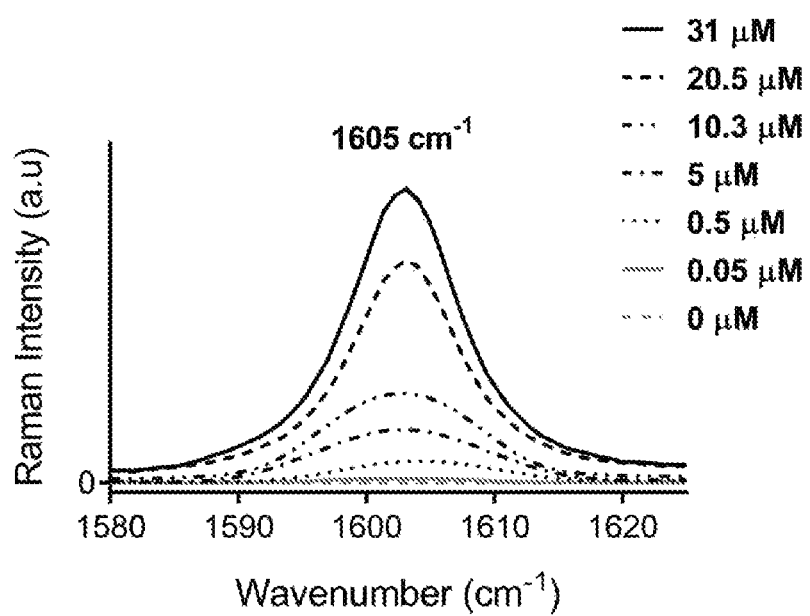
FIG. 11 shows Hp concentration dependent SERS spectra of TMB$^{2+}$. Au colloids were added and mixed before taking SERS measurement.
Figure 12:
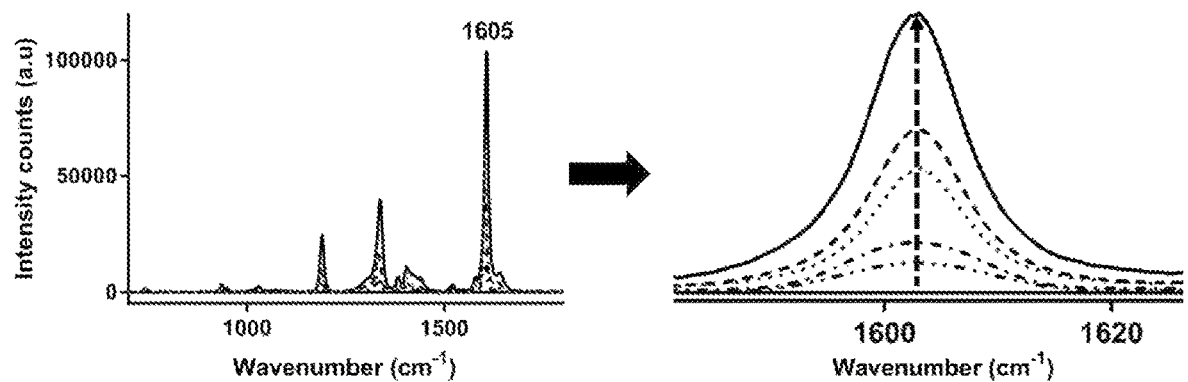
FIG. 12 shows the relationship between SERS intensity of TMB$^{2+}$ with different Hp concentration of FIG. 11. Gold colloids were mixed before taking SERS measurement. The flat line represents the TMB reactant.

Clearly, the Raman bands or peaks were significantly enhanced in the presence of Au colloids because of the adsorption of $TMB^{2+}$ onto the surface of gold nanoparticles. With increasing concentration of [Hp-Hb] complex, the SERS signal intensity from $TMB^{2+}$ also increased and there was a linear correlation between the SERS signal intensity and Hp concentration from 50 nM to 31 µM (see FIG. 11 which shows Hp concentration dependent SERS spectra of $TMB^{2+}$). The Raman spectra of various Hp concentrations with $TMB^{2+}$ product after mixing with gold colloids are shown in FIG. 12. The relationship between the adsorption and the concentration was found to be proportional in the present antibody free method for SERS based Hp detection. Therefore, the employment of SERS techniques in colorimetric assays serves a promising sensitive technique for Hp detection.

Observably, the lowest detection limit of 50 nM was 100 times better than that observed with colorimetric method. This confirms the sensitivity of SERS over UV absorbance/colorimetric methods.

Example 13

Results and Discussion For Effect of pH on SERS Detection

Figure 13:
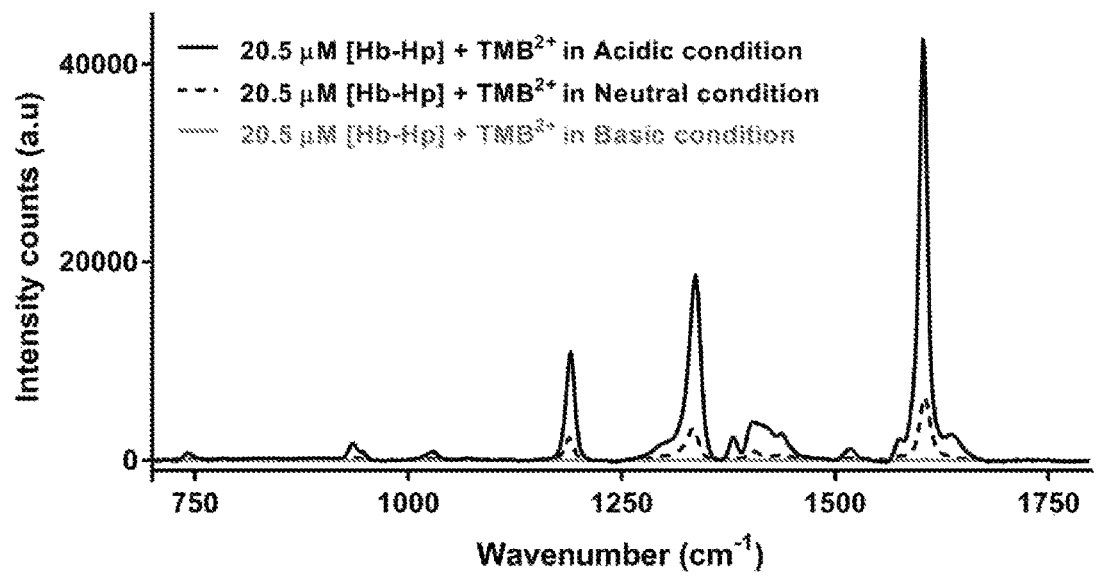
FIG. 13 shows a comparison of the SERS spectra for TMB$^{2+}$ at different pH conditions. From the comparison, it can be confirmed TMB$^{2+}$ shows stronger SERS activity only at low pH (acidic) condition.

In order to determine whether pH environment has any effect on the signal intensity of $TMB^{2+}$, SERS activity of the $TMB^{2+}$ with the same concentration of [Hb-Hp] complex at different pH conditions were measured. Based on the experiment, it was found that only at acidic conditions (e.g. pH of 2.6), $TMB^{2+}$ SERS signal was stronger. This was followed by neutral pH of 7, and finally at high pH conditions of more than 10, no SERS activity was found due to the absence of $TMB^{2+}$ charge transfer complex. This confirms that only at low pH conditions, stable $TMB^{2+}$ product is formed. FIG. 13 shows a comparison of the SERS spectra for $TMB^{2+}$ at different pH conditions. Based on FIG. 13, it was further confirmed that $TMB^{2+}$ shows strong SERS activity only at low pH (acidic) condition.

Further, to ascertain whether [Hb-Hp] complex provides any interference with SERS signal that adds up to $TMB^{2+}$ signal, two samples were tested. One of the samples was with TMB peroxidase reactant and the second without TMB.

Figure 14:
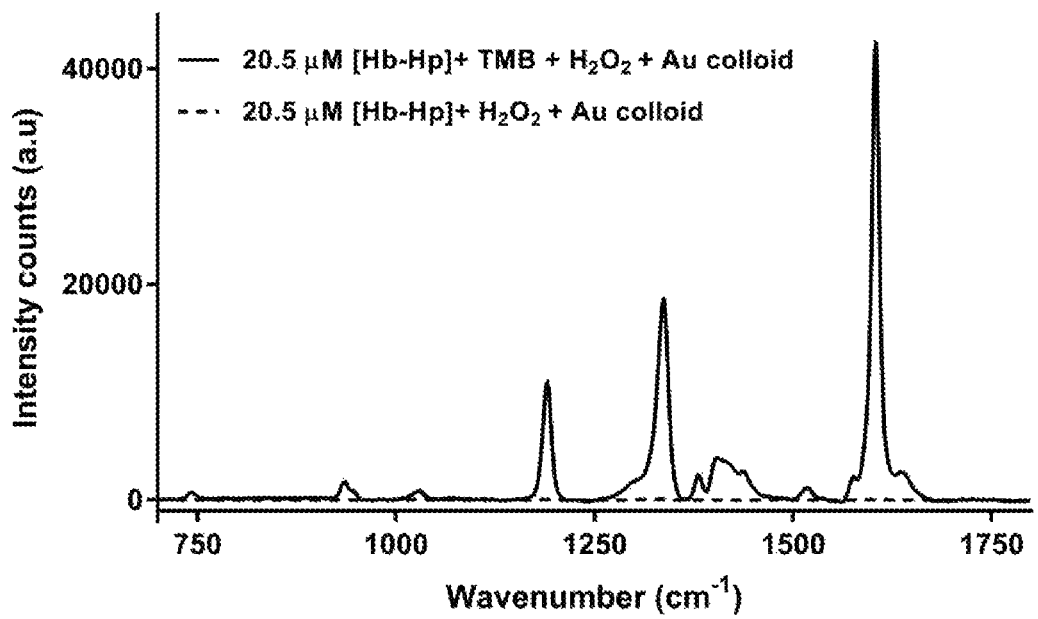
FIG. 14 shows a comparison of the SERS spectra for [Hb-Hp] complex in the presence and absence of TMB peroxidase reactant. From the comparison, it can be confirmed that [Hb-Hp] complex in the presence of Au colloid without TMB does not exhibit Raman activity and hence no SERS signal is observed.

Enzymatic reaction was allowed to take place. Finally, both samples were measured for SERS activity in the presence of Au colloids. As shown in FIG. 14, [Hb-Hp] complex in presence of Au colloid did not show any Raman activity, and hence, no SERS signal was observed. Meanwhile, the sample with TMB showed strong SERS activity due to formation of $TMB^{2+}$. Similarly, it was experimentally confirmed there was no competing peroxidase reaction possible in the absence of Hp through any other biological agent present in the cyst fluid (see FIG. 15). Here, the reaction mixtures with cyst fluid and peroxidase-reactant TMB with $H_2O_2$ in the presence and absence of Hb to form [Hb-Hp] complex were tested. The results showed only the sample with Hb in it could undergo peroxidase reaction to form Raman-active $TMB^{2+}$ due to the formation of [Hb-Hp] complex. The second sample without Hb did not undergo a peroxidase reaction.

Figure 15:
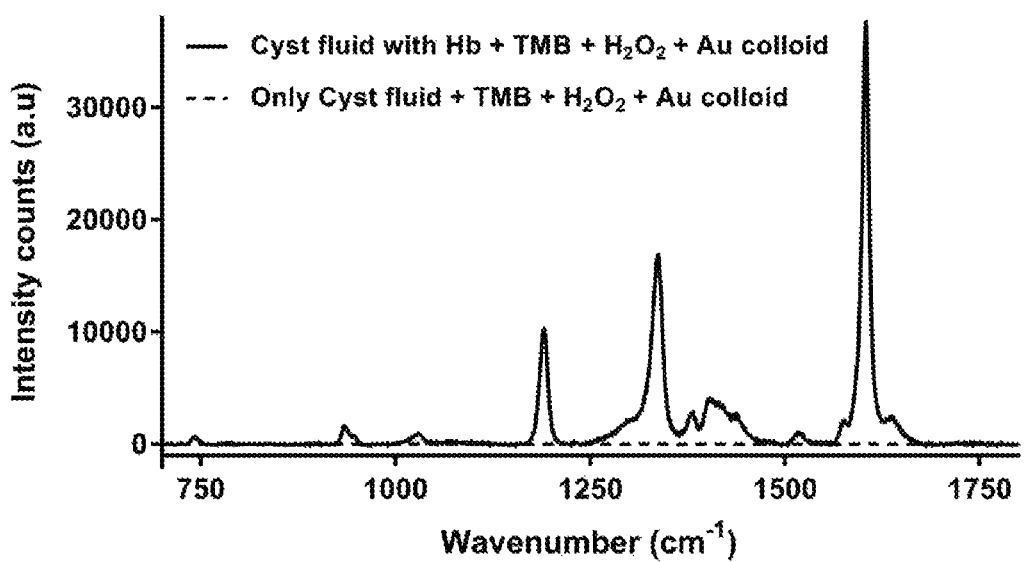
FIG. 15 shows a comparison of the SERS spectra for ovarian cyst fluid in the presence and absence of Hb (to form [Hb-Hp] complex) in reaction with TMB peroxidase reactant. From the above spectrum, it is clear that no other biological agent was involved in the peroxidase reaction other than [Hb-Hp] complex.

FIG. 15 shows a comparison of the SERS spectra for ovarian cyst fluid in the presence and absence of Hb (to form Hb-Hp complex) in reaction with TMB peroxidase reactant. From the spectrum, it is clear that no other biological agent was involved in the peroxidase reaction other than [Hb-Hp] complex.

Example 14

Results and Discussion for Comparison Between Colorimetric Assays and the Present Colorimetric Converted SERS Method Colorimetric assays typically require multiple steps, each with separate reagents. Each analysis needs a separate distinct reaction which utilizes long reaction time. In addition, they are not highly sensitive and need further confirmation by histological studies. On the other hand, the present modified SERS method for studying the colorimetric assay is highly sensitive due to the use of SERS platforms or substrates, e.g. Au colloids, which can enhance the intrinsic Raman signal from the chromogen by several fold, thereby allowing the detection and quantification of very low concentrations of Hp present in the sample. The advantages of the present SERS based method over existing colorimetric method are provided in Table 1 below.

TABLE 1

Comparison Between Colorimetric Method (ELISA) And Present SERS Based Method

| Colorimetric Method (ELISA) | Present Colorimetric Converted SERS Method |
| --- | --- |
| UV absorbance method | SERS based method |
| Needs very long experiment time | Very short experiment time (less than 10 minutes) |
| Calibration done using any source of haptoglobin along with its corresponding primary and secondary antibodies. | Calibration done using human haptoglobin and can be extendable to any source like porcine or canine haptoglobin etc. |
| Secondary antibody is required for signal amplification and this also results in nonspecific binding | No antibody may be required |
| Needs 7 to 8 steps and takes more than 1.5 hours | Involves only 3 steps with total time of less than 10 minutes required |
| Needs large sample volume for measurement in the order of several hundred μl. | Needs around 5 μl sample for doing SERS measurement |

Example 15

Results and Discussion For Quantification of Hp in Clinical Ovarian Cyst Fluid Samples As the product of the enzymatic reaction resulted in a concentration dependent increase in SERS signal intensity, of the three peaks that were used to identify $TMB^{2+}$, the SERS intensity at the steadily increasing prominent peak of 1605 $cm^{-1}$ was chosen to plot a standard calibration plot (see FIG. 3). The calibration plot shows linear regression with a $R^2$ value of 0.98.

Figure 16:
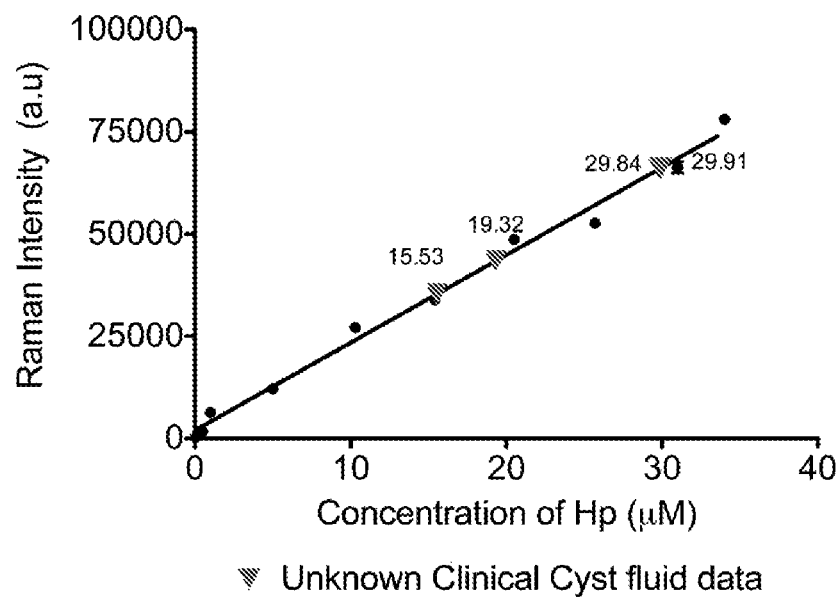
FIG. 16 shows a calibration plot for different concentrations of Hp present in the [Hb-Hp] complex based on the intensity of 1605 cm$^{-1}$ peak and the interpolation of unknown Hp concentration of cyst fluid from the calibration plot.

Four unknown clinical ovarian cyst fluid samples were tested for the concentration of Hp using the method mentioned above. The SERS intensity data of the unknown samples containing different concentrations of Hp are interpolated into the calibration plot as shown in FIG. 16. FIG. 16 shows a calibration plot for different concentration of Hp present in the [Hb-Hp] complex based on the intensity of 1605 $cm^{-1}$ peak and the interpolation of unknown Hp concentrations of cyst fluid from the calibration plot. The resultant Hp concentration were calculated as shown in Table 2 below, on the basis of a linear calibration curve represented by Y=2159X+1613.

TABLE 2

Comparison of ELISA Results with SERS Data Obtained from Four Clinical Samples with their Corresponding Histological Data

| Samples | Hp Concentration by ELISA (μM) | Hp Concentration by SERS (μM) | Histology Results |
| --- | --- | --- | --- |
| 1.1183 | 1.2 | 29.84 | Malignant: Serous papillary adenocarcinoma |
| 1.1184 | 8.2 | 29.91 | Malignant: Clear cell carcinoma |
| 1.1187 | 0.83 | 15.53 | Benign: Mucinous cystadenoma |
| 1.1188 | 3.2 | 19.32 | Benign: Mucinous cystadenoma |

Results of Hp concentration in the clinical samples are tabulated in Table 2 together with the inference from the histology data. From the above table, it is clear that SERS based antibody free method could quantify overall Hp present in the clinical sample irrespective of its phenotype, i.e. Hp(1-1), Hp(2-1) and Hp(2-2), whereas commercial ELISA kit is capable of quantifying just one specific phenotype due to the use of corresponding monoclonal antibody. This may be the reason behind the difference in Hp values between ELISA and SERS methods. Based on the results, it can be speculated that the cut-off Hp concentration may be in the range of 23 to 28 μM. This range was based on the very few clinical samples tested in which the benign samples had Hp concentration in the range of 15 to 20 μM, whereas for the malignant samples, the Hp concentration was 29 μM and above.

The advantages of the present method include short measurement time of less than 10 minutes and the ability to be measured on a portable compact Raman system. This type of bioassay can be extremely useful in operation theatres where the surgeons performing ovarian cystectomy can verify their intra-operative suspicion of malignancy. Ovarian malignancy is unexpectedly encountered in 1 to 14% of patients undergoing laparoscopic cystectomy. For patients who are still young and want to maintain their fertility, this method will be highly useful for deciding upon the suitable surgical procedures. A bench top portable Raman system is developed in FIG. 17. The prospect of translatability of this method to the clinics is very high.

Example 16

Portable Raman Microscope System Developed Based on Present SERS Based Method

Figure 17:
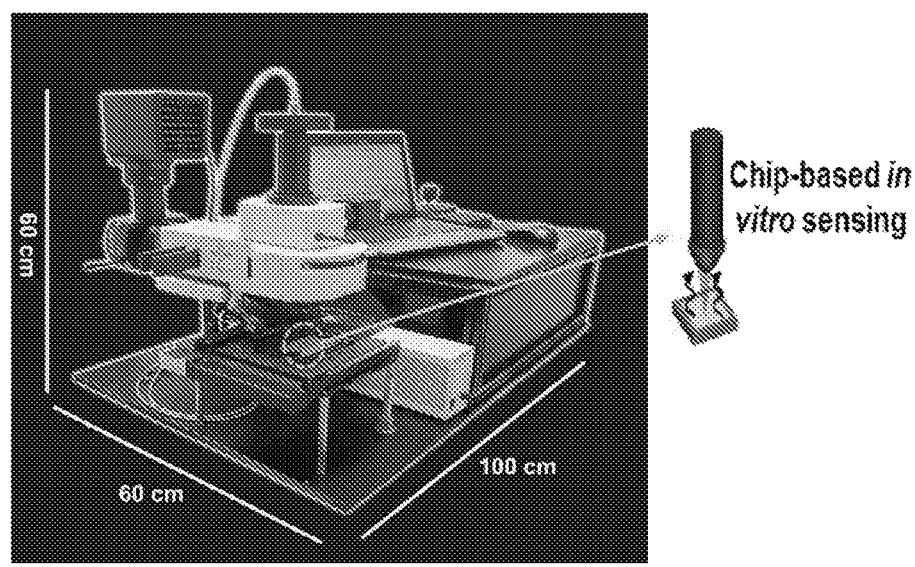
FIG. 17 shows a portable compact Raman setup with inbuilt 633 nm diode laser with ultra-high sensitive Spectrophotometer as detector.

In order to use the present method at bedside, a portable Raman microscope system was developed for fast and reliable SERS based detection and quantification of Hp in ovarian cyst fluid so that the present method could be translated to clinical application. As an initial step, an in-house portable compact Raman system have been designed and assembled as shown in FIG. 17. FIG. 17 shows the portable compact Raman setup with inbuilt 633 nm diode laser with ultra-high sensitive spectrophotometer as detector.

Example 17

Modification of ELISA Kits to Utilize the Present SERS Based Method

Using the peroxidase chemistry as described above, any ELISA kit can be designed into a SERS platform relying on the present method as disclosed herein. TMB or other peroxidase reagent which provides Raman active signal after oxidation can be used for this study.

Figure 18:
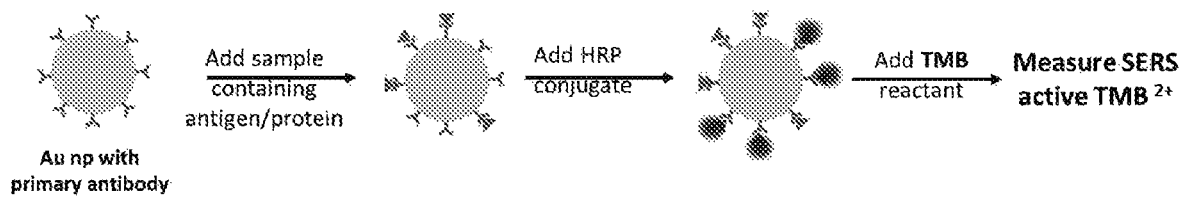
FIG. 18 is a schematic diagram showing the reaction flow for the protein/biomarker detection using standard ELISA approach. Au nanoparticles with primary antibodies are illustrated.
Figure 19:
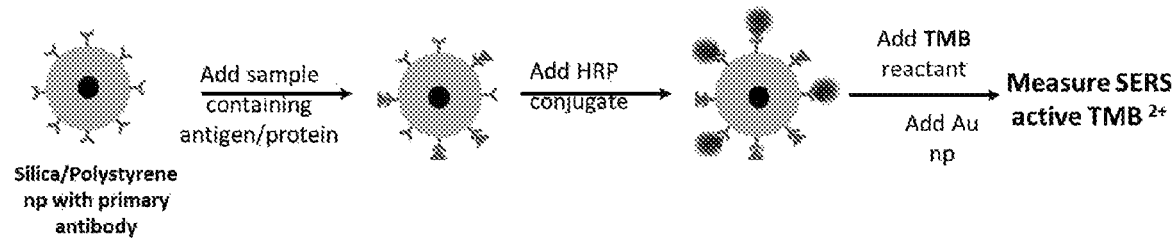
FIG. 19 is a schematic diagram showing the reaction flow for the protein/biomarker detection using standard ELISA approach. Silica/polystyrene nanoparticles with primary antibodies are illustrated.

In this example, a method for enhancing the sensitivity and reliability of analysis of proteins/biomolecules is described. This method incorporates the SERS methodology in which antibody bound gold nanoparticles were used to capture proteins/biomolecules of interest followed by incubation in horseradish peroxidase (HRP) conjugate which attaches to unbound antibodies. This robust and efficient analytical protocol leads to accurate quantification of proteins/biomolecules by means of peroxidase reaction. Protein quantification was done by analyzing a concentration-dependent SERS spectrum. FIG. 18 and FIG. 19 show the schematic diagrams of how measurements of SERS-active $TMB^{2+}$ are taken. FIG. 18 shows a sample suspected of containing antigens and/or proteins added to Au nanoparticles/colloids with primary antibodies. FIG. 19 shows a sample suspected of containing antigens and/or proteins added to silica/polystyrene nanoparticles with primary antibodies. HRP conjugate is then added in both schemes with the TMB reactant added thereafter. Based on these schematics, the present method is able to achieve a detection range from nM to µM and possesses a more sensitive detection limit compared with traditional chromogenic tests. Accordingly, the present SERS assay method as described herein can be extended to use for detection and quantification of various proteins and/or biomolecules.

With regard to the above, the SERS platform of the present method can be extended to detect or quantify any of the protein or biomarkers as long as an ELISA kit is specifically designed with the present method in mind For example, the same Hp detection method as discussed above can also be applied as a Hp antibody method as shown in FIG. 18. In this case, the gold colloid platform has been used to anchor the primary antibody/capturing agent. Instead of gold colloidal particles or nanoparticles, silica or polystyrene beads with a magnetic core can be employed as shown in FIG. 19. The size of the particles is in the range of micron to sub-micron diameter to anchor the primary antibody/capturing agent. In the context of the present disclosure, and particularly for this example, micron and sub-micron refers to silica or polystyrene beads containing a magnetic core, wherein the diameter of the beads are in the range of 1 to 10 µm and 100 nm to 300 nm, respectively. Meanwhile, in the case of gold, these refers to less than 100 nm gold colloids.

This platform is not only suitable with respect to Hp but also adoptable for various proteins or biomarkers (see FIG. 19 for details). According to FIG. 19, it is shown that the use of silica or polystyrene beads as anchoring agents helps in easy washing steps.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method for detecting an analyte using surface enhanced Raman spectroscopy (SERS), the method comprising
    a) contacting one or more analyte-binding molecules with the analyte under conditions that allow binding of the analyte to the one or more analyte-binding molecules to form a first mixture, wherein the analyte comprises haptoglobin and the one or more analyte-binding molecules comprise haemoglobin,
    b) contacting a liquid reagent comprising a peroxidase substrate and a peroxide source with the first mixture to form a second mixture, while maintaining pH of the second mixture at 10 or less,
    c) quenching the second mixture to form a third mixture,
    d) contacting the third mixture with a SERS-active substrate, and
    e) detecting a surface enhanced Raman signal from the third mixture and/or a surface of the SERS-active substrate,
    wherein the one or more analyte-binding molecules are attached to a support,
    wherein the support comprises a non-SERS active material or a SERS-active material, wherein the non-SERS-active material comprises an inorganic oxide particle having a magnetic core or a polymeric particle having a magnetic core, and wherein the SERS-active material comprises gold nanoparticles.

2. The method according to claim 1, wherein the one or more analyte-binding molecules further comprise an antibody.

3. The method according to claim 1, wherein contacting the one or more analyte-binding molecules with the analyte is carried out for a time period in the range of about 2 minutes to about 10 minutes.

4. The method according to claim 1, wherein pH of the first mixture is adjusted to be in the range of about 2.6 to about 2.8.

5. The method according to claim 1, wherein the peroxidase substrate is selected from the group consisting of 3,3',5,5'-tetramethylbenzidine, o-phenylenediamine, biphenyl-4,4'-dithiol, 5-bromo-4-chloro-3-indolyl phosphate, 2,2'-azino-bis(3-ethylbenzthiazoline-6-sulfonic acid), and combinations thereof.

6. The method according to claim 1, wherein the peroxide source is selected from the group consisting of hydrogen peroxide, carbamide peroxide, sodium perborate, sodium percarbonate, urea peroxide, and combinations thereof.

7. The method according to claim 1, wherein pH of the second mixture is maintained in the range of about 2.6 to about 2.8.

8. The method according to claim 1, wherein contacting the liquid reagent with the first mixture is carried out for a time period in the range of about 1 minute to about 5 minutes.

9. The method according to claim 1, wherein quenching the second mixture is carried out by at least one of heating the second mixture or adding a quenching agent to the second mixture.

10. The method according to claim 9, wherein heating the second mixture is carried out at a temperature in the range of about 80° C. to about 95° C.

11. The method according to claim 9, wherein the quenching agent is selected from the group consisting of hydrochloric acid, sulfuric acid, saponins, sodium dodecyl sulfate, cetyl trimethyl ammonium bromide, N-laurylsarcosine, dodecyltrimethylammonium bromide, 8-anilino-1-naphthalenesulfonic acid, protoporphyrin, bilirubin, taurodeoxycholic acids, dicoumarol, 2-mercaptobenzothiazole, catalase enzyme, and combinations thereof.

12. The method according to claim 1, wherein the SERS-active substrate comprises gold nanoparticles.

13. The method according to claim 12, wherein the gold nanoparticles are attached on a chromatographic paper.

14. The method according to claim 1, wherein the SERS-active substrate comprises
   a) a plurality of nanostructures attached on a support, and
   b) a first metallic layer deposited on the plurality of nanostructures.

15. The method according to claim 14, wherein the SERS-active substrate further comprises a second metallic layer deposited on the first metallic layer to form a metallic bilayer.

16. The method according to claim 15, wherein the first metallic layer and the second metallic layer are independently gold or silver.

17. The method according to claim 16, wherein the first metallic layer is silver, and the second metallic layer is gold.

18. The method according to claim 1, wherein the analyte is contained in a sample, wherein the sample is a bodily fluid and the detection is in vitro.

19. The method according to claim 1, wherein the surface enhanced Raman signal from the third mixture and/or the surface of the SERS-active substrate is correlated with amount of the analyte.

* * * * *